(12) United States Patent
Rowland et al.

(10) Patent No.: US 10,226,218 B2
(45) Date of Patent: Mar. 12, 2019

(54) PRESSURE SENSING IMPLANT

(71) Applicant: ENDOTRONIX, INC., Woodridge, IL (US)

(72) Inventors: Harry Rowland, Plainfield, IL (US); Michael Nagy, Lawrenceville, GA (US); Balamurugan Sundaram, Dunlap, IL (US); Suresh Sundaram, Dunlap, IL (US)

(73) Assignee: ENDOTRONIX, INC., Woodridge, IL (US)

( * ) Notice: Subject to any disclaimer, the term of this patent is extended or adjusted under 35 U.S.C. 154(b) by 426 days.

(21) Appl. No.: 14/777,654

(22) PCT Filed: Mar. 17, 2014

(86) PCT No.: PCT/US2014/030661
§ 371 (c)(1),
(2) Date: Sep. 16, 2015

(87) PCT Pub. No.: WO2014/197101
PCT Pub. Date: Dec. 11, 2014

(65) Prior Publication Data
US 2016/0029956 A1 Feb. 4, 2016

Related U.S. Application Data

(63) Continuation-in-part of application No. 14/129,725, filed as application No. PCT/US2012/044998 on Jun. 29, 2012, now Pat. No. 9,867,552.
(Continued)

(51) Int. Cl.
*A61B 5/00* (2006.01)
*A61B 5/0215* (2006.01)
*A61B 5/07* (2006.01)

(52) U.S. Cl.
CPC ............ *A61B 5/686* (2013.01); *A61B 5/0215* (2013.01); *A61B 5/076* (2013.01); *A61B 2562/0247* (2013.01); *A61B 2562/168* (2013.01)

(58) Field of Classification Search
None
See application file for complete search history.

(56) References Cited

U.S. PATENT DOCUMENTS 4,026,276 A   5/1977   Chubbuck
5,454,270 A   10/1995   Brown et al.
(Continued)

FOREIGN PATENT DOCUMENTS

CA   2840645 A1   1/2013
CN   1701464 A    11/2005
(Continued)

OTHER PUBLICATIONS

Patent Cooperation Treaty (PCT), International Search Report and Written Opinion for Application PCT/US12/44998, dated Sep. 25, 2012, 9 pgs., International Searching Authority, US.
(Continued)

*Primary Examiner* — Michael R Bloch
(74) *Attorney, Agent, or Firm* — McDonald Hopkins LLC

(57) ABSTRACT

A wireless circuit includes a housing having at least one opening, and sensor connected to the housing at the opening. The sensor includes a first layer having a first dimension and a second layer having a second dimension shorter than the first dimension. The second layer may be positioned entirely within the housing and a surface of said first layer may be exposed to an exterior of the housing.

15 Claims, 17 Drawing Sheets

Related U.S. Application Data

(60) Provisional application No. 61/502,982, filed on Jun. 30, 2011, provisional application No. 61/786,793, filed on Mar. 15, 2013.

(56) References Cited

U.S. PATENT DOCUMENTS

| | | | |
|---|---|---|---|
| 5,510,276 | A | 4/1996 | Diem et al. |
| 5,840,148 | A | 11/1998 | Campbell et al. |
| 6,111,520 | A * | 8/2000 | Allen ................. B60C 23/0408 324/655 |
| 6,939,299 | B1 * | 9/2005 | Petersen ................. A61B 3/16 600/300 |
| 7,174,212 | B1 | 2/2007 | Klehn et al. |
| 7,401,521 | B2 | 7/2008 | Bellini et al. |
| 7,574,792 | B2 | 8/2009 | O'Brien et al. |
| 7,662,653 | B2 * | 2/2010 | O'Brien ................. B81B 7/007 257/E21.499 |
| 7,686,762 | B1 | 3/2010 | Najafi et al. |
| 7,763,487 | B2 | 7/2010 | Villa et al. |
| 8,132,465 | B1 | 3/2012 | Doelle et al. |
| 8,154,389 | B2 | 4/2012 | Rowland et al. |
| 8,493,187 | B2 | 7/2013 | Rowland et al. |
| 8,506,495 | B2 * | 8/2013 | Mi ....................... A61B 5/0031 600/481 |
| 9,078,563 | B2 * | 7/2015 | Cros .................... A61B 5/0215 |
| 9,305,456 | B2 | 4/2016 | Rowland et al. |
| 2005/0121734 | A1 * | 6/2005 | Degertekin .......... A61B 5/0215 257/414 |
| 2006/0109188 | A1 | 5/2006 | Ikeda et al. |
| 2006/0137461 | A1 | 6/2006 | Bellini et al. |
| 2006/0177956 | A1 | 8/2006 | O'Brien et al. |
| 2006/0241354 | A1 | 10/2006 | Allen |
| 2006/0287602 | A1 | 12/2006 | O'Brien et al. |
| 2007/0163355 | A1 | 7/2007 | Nassar et al. |
| 2007/0208390 | A1 | 9/2007 | Von Arx et al. |
| 2007/0267708 | A1 | 11/2007 | Courcimault |
| 2008/0269573 | A1 | 10/2008 | Najafi et al. |
| 2008/0269829 | A1 | 10/2008 | Li et al. |
| 2009/0221885 | A1 | 9/2009 | Hall et al. |
| 2011/0046452 | A1 | 2/2011 | Najafi et al. |
| 2011/0063088 | A1 | 3/2011 | Stevenson et al. |
| 2014/0028467 | A1 | 1/2014 | Nagy et al. |
| 2014/0155710 | A1 | 6/2014 | Rowland et al. |
| 2014/0306807 | A1 | 10/2014 | Rowland et al. |

FOREIGN PATENT DOCUMENTS

| | | |
|---|---|---|
| CN | 1826686 A | 8/2006 |
| CN | 101128957 A | 2/2008 |
| CN | 101278439 A | 10/2008 |
| CN | 101427923 A | 5/2009 |
| JP | 2000005136 A | 1/2000 |
| JP | 2002515278 A | 5/2002 |
| JP | 2003144417 A | 5/2003 |
| JP | 2005284511 A | 10/2005 |
| JP | 2006309582 A | 11/2006 |
| JP | 2007256287 A | 10/2007 |
| JP | 2008022935 A | 2/2008 |
| JP | 2010538254 A | 12/2010 |
| WO | 2009146089 A1 | 12/2009 |
| WO | 2012015955 A1 | 2/2012 |

OTHER PUBLICATIONS

Extended European Search Report for Application 12804636.4 PCT/US2012044998, dated Jan. 20, 2015, 6pgs., Eurpoean Patent Office, Germany.

Patent Cooperation Treaty (PCT), International Search Report and Written Opinion for Application PCT/US/14/30661, dated Sep. 17, 2015, 8 pp., International Searching Authority, US.

Extended European Search Report for Application 14806873.7 PCT/US2014030661, dated May 20, 2016, 7 pp., European Patent Office, Germany.

* cited by examiner

PRESSURE SENSING IMPLANT

CROSS-REFERENCE TO RELATED APPLICATIONS

This application claims priority to Provisional Patent Application No, 61/786,793 entitled "PRESSURE SENSING IMPLANT," filed on Mar. 15, 2013 and PCT Application No. PCT/US2014/030661, filed on Mar. 17, 2014, entitled "PRESSURE SENSING IMPLANT". This application is a continuation-in-part of U.S. patent application Ser. No. 14/129,725 entitled "IMPLANTABLE SENSOR ENCLOSURE WITH THIN SIDEWALLS," filed on Dec. 27, 2013, which claims priority to International Patent Application No. PCT/US/2012/044998 entitled "IMPLANTABLE SENSOR ENCLOSURE WITH THIN SIDEWALLS," filed on Jun. 29, 2012 which claims priority to Provisional Patent Application No. 611502,982 entitled "IMPLANTABLE SENSOR ENCLOSURE WITH THIN SIDEWALLS," filed on Jun. 30, 2011, each of which are hereby incorporated by reference in its entirety.

FIELD OF INVENTION

This application relates to implant packages and more particularly to an implantable sensor enclosure for optimal wireless communication.

BACKGROUND

Implantable wireless sensors are useful in assisting diagnosis and treatment of many diseases. Examples of wireless sensor readers are disclosed in U.S. patent application Ser. No. 12/737,306 and U.S. Pat. No. 8,154,389B2, both entitled Wireless Sensor Reader, which are incorporated by reference herein. Delivery systems for wireless sensors are disclosed in PCT Patent Application No. PCT/US2011/45583 entitled Pressure Sensor, Centering Anchor, Delivery System and Method, which is also incorporated herein by reference. In particular, there are many applications where measuring pressure from within a blood vessel deep in a patient's body is clinically important. For example, measuring the pressure in the heart's pulmonary artery is helpful in optimizing treatment of congestive heart failure. In this type of application, a sensor may need to be implanted 10 to 20 cm beneath the surface of the skin.

Implantable wireless sensors that use radiofrequency (RF) energy for communication and/or power have been found to be particularly useful in medical applications. However, there are many tradeoffs and design constraints in designing such implantable sensors, such as size, cost and manufacturability.

A key challenge in successful commercialization of these implantable wireless sensors is the design tradeoff between implant size and the "link distance", which is the physical distance between the implant and the external device communicating with the implant. From a medical standpoint, it is desirable for an implant to be as small as possible to allow catheter based delivery from a small incision, implantation at a desired location, and a low risk of thrombosis following implant. However, from a wireless communication standpoint, the smaller the implant, the shorter the link distance. This distance limitation is driven primarily by the size of the antenna that can be realized for a given overall implant size. A larger antenna is better able to absorb RF energy and transmit RF energy than a smaller antenna. For example, in the case of wireless communication via inductive coupling, a typical implant antenna has the form of a coil of wire. The coil's "axis" is the line that extends normal to the plane of the windings, i.e. the axis is perpendicular to the wire's length. As the area encircled by the coil increases, the amount of magnetic flux that passes through it generally increases and more RF energy is delivered to/received from the implant. This increase in flux through the implant antenna can result in an increase in link distance. Thus to achieve maximum link distance for a given implant size, the implant antenna should be of maximal size.

While antenna size is important, other implant architectures may benefit from maximizing the size of other internal components. An implant containing an energy storage device such as a battery, for example, would enjoy longer battery lifetime with a larger battery. In another example, a drug-eluting implant could hold a larger quantity of the drug. Other examples will be apparent to those skilled in the art.

Moreover, an optimal implantable sensor may be best designed to function with a specific device or reader device. Wireless transmitter and reader devices, such as the wireless reader of U.S. patent application Ser. No. 13/423,693 entitled "WIRELESS SENSOR READER," which is hereby incorporated by reference herein in its entirety, may require a specific implantable sensor to provide optimal functionality of the reader/sensor system. An optimal implantable sensor for such systems may be configured to transduce pressure into a resonant frequency. The sensor may be a passive sensor with no internal power source, such as a sensor having an LC resonant tank circuit. The sensor may minimize its total size while maximizing coil area, as described in PCT Patent No. PCT/US2012/044998 entitled "IMPLANTABLE SENSOR ENCLOSURE WITH THIN SIDEWALLS," which is hereby incorporated by reference herein in its entirety. The sensor may have a high RF Quality (Q factor), which is maximized by careful materials selection and device design. The sensor may be immune to temperature changes, including temperature changes during the manufacturing process and in transition between air and in vivo. The sensor may have high sensitivity and good electrical isolation between electrical nodes and surrounding body fluids or tissue. The sensor may be highly stable over time, have good mechanical strength, incorporate biocompatible materials, and minimize use of ferrite materials.

For an LC type wireless MEMS sensor, overcoming these challenges requires the design of a small sensor with high resonant quality factor (Q) at low operating frequencies (the human body attenuates wireless data signals, with generally more signal attenuation occurring at higher frequencies above 50 MHz). An additional challenge arises due to regulatory policies and licensed frequency bands for commercial use. With current technology, it is difficult to reliably fabricate an accurate ultra-miniature implantable wireless pressure sensor with high quality factor at low operating frequencies within a tightly controlled operating range. To achieve high resonant Q in an LC circuit requires both an inductor and a capacitor with high Q. Using multiple turns of coils with large cross sectional area conductors is one of the factors that improves the Q of an inductor. A high Q capacitor is generally formed by closely spaced low resistance conductors separated by a dielectric material with low dielectric loss.

While an ultra-miniature sensor requires an inductor with high Q to ensure reliable wireless signal communication at appropriate distance between sensor and external device, a high Q inductor places limitations on overall sensor size. In known LC sensors, the placement and design of a high Q inductor restricts the location and size of the capacitive sensor. In known implantable pressure sensors, the active capacitance areas (the areas where capacitance changes with pressure changes) of capacitive sensors are realized by large solid area electrodes, Known capacitive sensors must reside entirely outside the area defined by an inductor. For example, FIG. 1A shows a sensor 10' having a capacitor 12' outside of an inductor spiral coil 14. FIG. 1B shows a sensor 10' having a capacitor 12' inside the center of an inductor spiral coil 14. The capacitor 12', however, cannot overlap an inductor spiral coil 14, as shown in FIG. 1C, without significantly reducing the quality factor of the LC sensor. Furthermore, placement of the capacitor 12' near the inner turns of the inductor spiral coil 14 may also significantly reduce the quality factor of the LC sensor. Also, placement of the capacitor electrodes on the plane of or near the inductor can reduce the quality factor of the LC sensor. Thus in known sensors, capacitors are placed adjacent to an inductor, which increases the size of the sensor, or inside the central area of the spiral inductor with significant space between the inner turns of the spiral inductor and the edges of the capacitor plates, which limits the size of the capacitor and/or the size of the inductor.

Known wireless pressure sensors are also limited by having a capacitive sensor that does not have a high Q. In known implantable pressure sensors, capacitive sensors are realized by large solid area electrodes. This capacitance design is not optimal and results in a low quality factor capacitance for high frequency alternating currents. Large solid area electrodes of a capacitor when not positioned away from the inductor result in reduced quality factor of an LC circuit due to eddy currents in the capacitor electrode when the electrode is subject to high frequency alternating currents.

There are further challenges with known sensors to realize a sensor that operates within approved frequency ranges for wireless signal transmission and at the same time experiences minimal signal attenuation through the human body. To operate sensors at low frequencies, which experience low signal attenuation, requires a large value of capacitance and large value of inductance. Both inductance and capacitance are limited by size. A large inductance can be achieved by large spiral turns of a conductor. Large capacitance can be achieved by large area capacitor electrodes separated by a small gap. If the size of the capacitor electrodes are limited by the inductor and the size of the sensor, the electrodes must be spaced closer together to achieve high capacitance. Controllably fabricating electrodes with a small gap within practical manufacturing tolerances is challenging and could result in a lower breakdown voltage between the electrodes, stiction of the electrodes, limited pressure operating range, and low yield or high cost.

During the fabrication of MEMS sensors, dimensional tolerances may vary spatially over a wafer and may additionally vary from one wafer to another. The variation in component dimensions affects the properties of the resulting device. In many cases, it is difficult to tightly control the capacitance of a sensor within an economical production environment. With known LC sensors, the operating range of the passive sensor cannot be modified after fabrication of the device as often both the capacitor and the inductor are sealed from the environment. Such designs require operation of the devices over larger operating ranges to account for manufacturing tolerances and these ranges may not be approved for commercial use by regulatory bodies. Other current methods to tune the operating range of a sensor after fabrication requires on chip calibration efforts which can increase the size of the sensor and/or the power consumption of the sensor which reduces the usefulness of the sensor. With current technology, it is difficult to fabricate a small sensor that can operate in a specified operating range at low frequencies. The ability to tune the operating range of a sensor after fabrication can increase device yields so that producing wireless sensors within allowable regulated areas is economically feasible.

Another challenge in commercialization of implantable wireless sensors is the need to protect the sensitive sensor electronics from potentially corrosive or damaging fluids of the body. For many implant applications, the sensor may need to record accurate measurements for a period of time exceeding 7 to 10 years. Small changes in electrical, chemical, or mechanical properties of the implant over this time period can result in inaccurate measurements. To prevent inaccurate measurements, a hermetic enclosure may be required to protect the sensitive electronics of the sensor from the transfer of liquids and gases from the bodily environment.

Hermetic enclosures for implants are typically constructed of metals, glasses, or other ceramics. Metals are malleable and machineable, capable of being constructed into thin walled hermetic enclosures such as the titanium enclosures of pacemakers. Unfortunately, the use of metals in hermetic enclosures may negatively impact the ability of the sensor to communicate wirelessly with an external device, especially when communication at low radiofrequencies is desired. While ceramics and glasses are compatible with wireless RF communication, it is difficult to machine ceramics to a thin walled hermetic enclosure. The brittleness of ceramics prevents the construction of thin wall hermetic enclosures from ceramic materials.

State of the art ceramic machining can produce walls of approximately 0.5-0.7 mm thickness. For implants whose length, width, and height dimensions are typically ones of millimeters, this can represent a significant reduction in available internal volume for components such as antennas.

Hermetic enclosures known in the art, particularly those made of ceramic and/or glass materials, do not lend themselves to efficient use of limited space. Non-metal hermetic enclosures known in the art are typically manufactured via planar processing technology, such as low temperature cofired ceramic processes, laser machining, ultrasonic machining, Electronic Discharge Machining (EDM), or Micro Electro Mechanical Systems (MEMS) fabrication techniques. These techniques are capable of processing ceramics and glasses with tight control of feature resolution. However, sidewalls of an implant package made with these techniques often require use of a dicing saw or laser to separate the implant package from the remaining substrate. Due to manufacturing constraints and the need for mechanical strength, implant package sidewalls made by these methods are typically 0.3 mm-0.5 mm thick. Alternative manufacturing approaches, such as the molding or machining of ceramic, are typically limited to minimum sidewalls of 0.5-0.7 mm thick.

An example of a prior art hermetic implant package 10 is shown in FIG. 1. The implant package 10 includes thick sidewalls 12 that limit the space available for the internal components, in this case implant antenna 14. For example, an implant package of width 4 mm that has sidewalls 0.5 mm thick only has a maximum of 3 mm of width available for an implant antenna. FIG. 1D shows an antenna 14 that is placed into the implant package from an opening at the top of the package. To complete the implant package, a top layer 16 is connected or bonded to the implant package and sealed as shown in FIG. 2A. For pressure-sensing implant packages known in the art, the top layer is typically either a capacitive pressure sensor itself, a thin membrane that is directly part of a sensing electronic circuit, or a thin membrane that communicates pressure from the environment to the inside of the implant package via an incompressible liquid or gel. Manufacturing techniques known in the art are capable of routinely processing membranes to thicknesses of 0.025-0.1 mm. Many variations of the FIG. 1D-2 architecture exist in the prior art, including the method of etching a cavity in half of a housing to create the thin wall on top of the coil, and then bonding the two housing halves vertically. This is depicted in the sketch of FIG. 2B, where the upper housing half 999 has a cavity etched into it to create the thin membrane.

Other prior art exemplifies wireless implant architectures of the type shown in FIG. 1D and FIG. 2, where the thin pressure sensitive membrane is in a plane that is perpendicular to the coil's axis. U.S. Pat. No. 7,574,792 (O'Brien), U.S. Pat. No. 6,939,299 (Petersen), and U.S. Pat. No. 4,026,276 (Chubbuck) all teach implantable pressure sensors with coil antennas, and hermetic housings with at least one deformable pressure-sensitive wall. In all these cases, the pressure-sensitive walls of the housings are perpendicular to the coil axis, and the walls located outside the coil perimeter are rigid, structural, and relatively thick. In these architectures, total coil area is limited by the need for a relatively thick structural wall outside the coil perimeter.

To improve implantable wireless sensors, it is desirable to have a hermetic enclosure with thin walls outside the coil antenna perimeter, thus maximizing the internal dimension that most constrains antenna size.

SUMMARY OF THE INVENTION

This application relates to hermetically packaged wireless electronics and more particularly to an implantable sensor design and manufacturing approach to optimize manufacturability, size, longevity, RF characteristics, and overall performance.

In an embodiment, a wireless circuit includes a housing and at least one antenna coil wound about a coil axis within the housing. The coil axis may be substantially parallel to at least one wall of the housing, wherein the wall parallel to the coil axis is substantially thinner than other walls of the housing. The housing may be a hermetically sealed housing.

In an embodiment, the wireless circuit may be manufactured by forming a housing of a material with at least one open side. Electronics, including an antenna coil, may then be placed into the housing such that said antenna coil's axis is substantially parallel to the plane of at least one open side. A wall that is substantially thinner than the walls of the housing may then be bonded to the open side. The wall may be hermetically bonded or otherwise bonded as known in the art.

In an embodiment, the wireless circuit may be manufactured by forming a housing of a material with at least two open sides. Electronics, including an antenna coil, may then be placed into the housing. A sensor may be bonded to one of the open sides to form a wall on one of the sides. The sensor may be substantially thinner than the walls of the housing. A wall that is substantially thinner than the walls of the housing may be bonded to another open side. The walls may be hermetically bonded or otherwise bonded as known in the art.

In an embodiment, the wireless circuit may comprise a sensor with conductive features. The conductive features may be patterned in a solid area. The solid area may incorporate slots or otherwise breaks that result in a non-continuous solid area. The conductive features may comprise one or more electrodes of a capacitor, for example a capacitive pressure sensor. A capacitive pressure sensor with non-continuous conductive features over a solid area may be placed near an inductor coil or on or near an inductor coil to form a wireless circuit with small form factor and optimal RF quality factor.

In an embodiment, a circuit may comprise a housing having at least one opening, and sensor connected to the housing at the opening. The sensor may include a first layer having a first dimension and a second layer having a second dimension shorter than the first dimension. The second layer may be positioned entirely within the housing and a surface of said first layer may be exposed to an exterior of the housing.

BRIEF DESCRIPTION OF THE DRAWINGS

Embodiments of the present disclosure are described herein with reference to the drawings wherein.

DETAILED DESCRIPTION OF THE PREFERRED EMBODIMENTS

Reference will now be made in detail to embodiments of the invention, examples of which are illustrated in the accompanying drawings. It is to be understood that other embodiments may be utilized and structural and functional changes may be made without departing from the respective scope of the invention.

This application relates to implant packages and more particularly to an implantable sensor design and manufacturing approach to optimize manufacturability, size, longevity, RF characteristics, and overall performance. To facilitate maximum link distance for a given implant size, the enclosure should be constructed to maximize antenna coil area, while still providing ample protection.

Figure 1A:
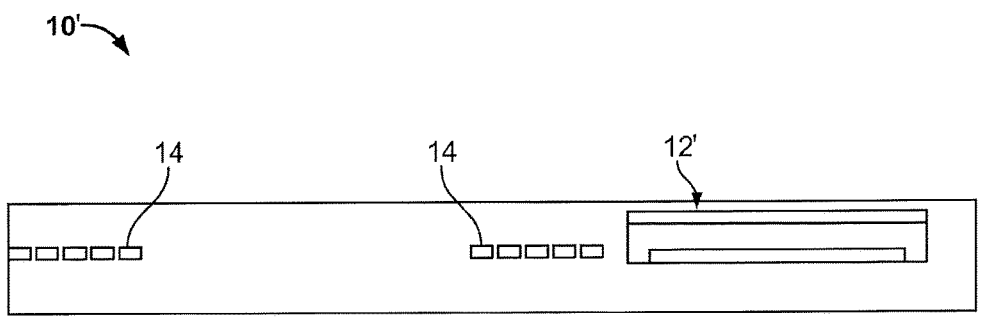
FIG. 1A illustrate a prior art implant package comprising a capacitor and inductor.
Figure 1B:
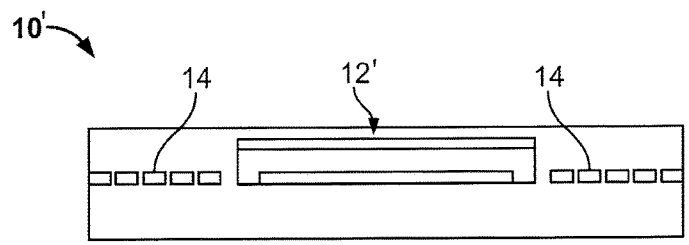
FIG. 1B illustrates another implant package comprising a capacitor and inductor.
Figure 1C:
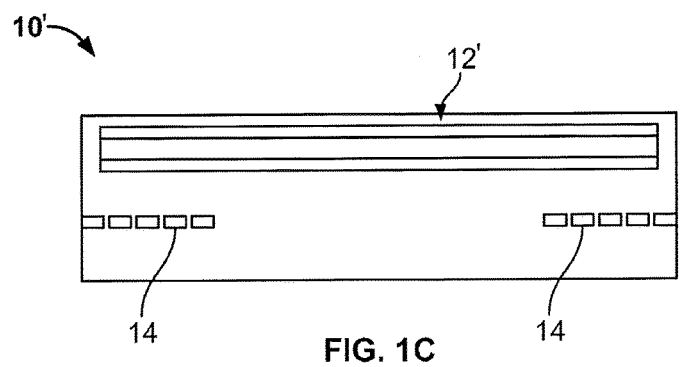
FIG. 1C illustrates another implant package comprising a capacitor and inductor.
Figure 1D:
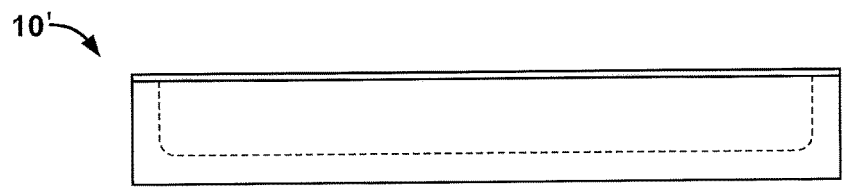
FIG. 1D illustrates a prior art implant package, not including the final sealing layer.
Figure 1D:
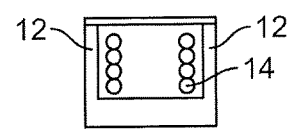
Figure 2A:
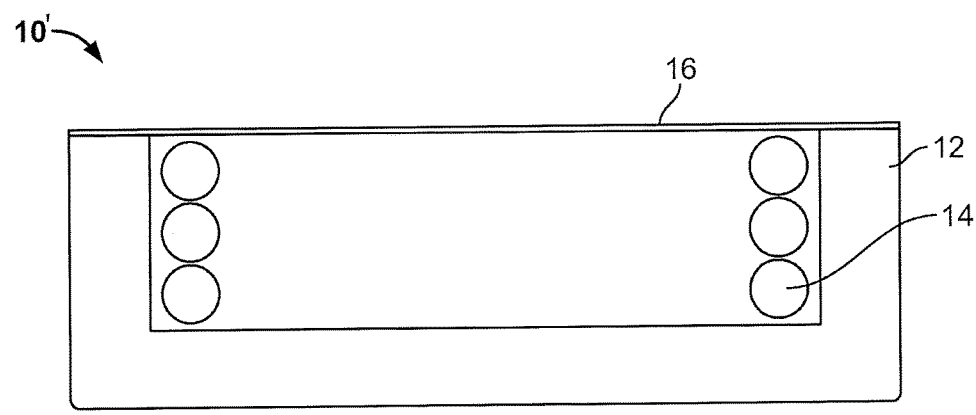
FIG. 2A illustrates a typical prior art implant package, including a thin sealing layer.
Figure 2B:
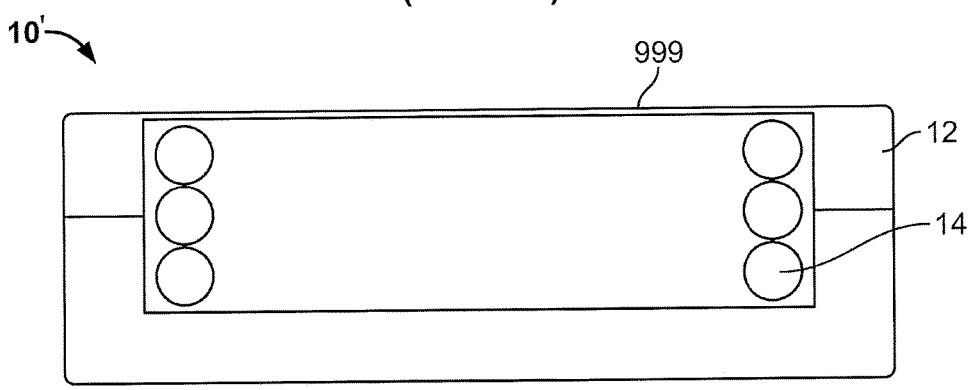
FIG. 2B illustrates a typical prior art implant package, with a cavity etched into part of the housing.

The implant package may utilize thin membrane materials such as glass, quartz, sapphire, fused silica, alumina, titanium, diamond, or other materials known in the art, to increase the space available inside an implant package of a fixed outer size. Whereas in prior art implant packages the thin membrane is bonded to the top of the implant package, as in FIGS. 1 and 2, the thin membrane or membranes may be bonded to the side of the implant package, such that they are in a plane substantially parallel with the axis of the coil, as in FIG. 3.

Figure 3A:
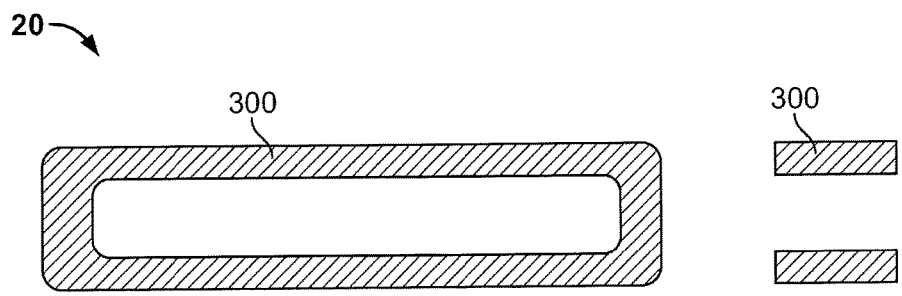
FIG. 3A illustrates the housing portion of a hermetic wireless package of the present invention.
Figure 3B:
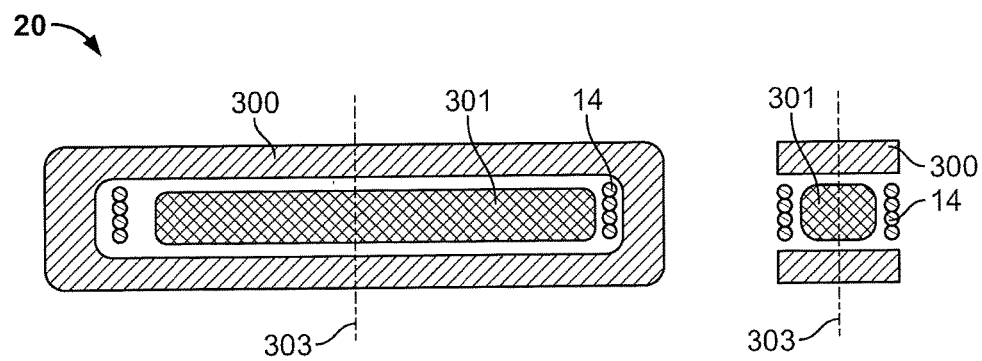
FIG. 3B illustrates the complete hermetic wireless implant of the present invention.
Figure 3C:
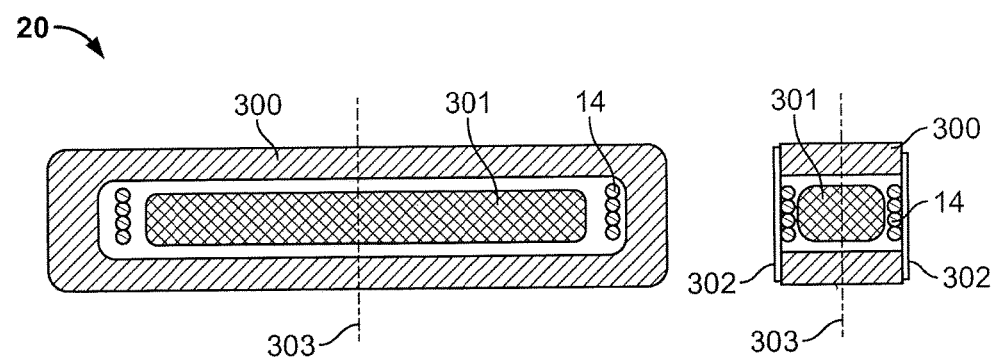
FIG. 3C illustrates a hermetic wireless implant having thin walls bonded to the housing.

FIGS. 3A-3C show basic assembly steps for a wireless implant package 20 that maximizes coil area by its wall arrangement. The implant in the Figure has the long, narrow, rectangular shape of a typical cardiovascular implant, although the principle applies to any geometry. FIG. 3A illustrates the basic housing 300 in side view (long dimension) and front view (short dimension) cutaway. In an embodiment, the dimension of housing 300 may be generally cuboid and defining a volume therein. The housing side walls may be of specific dimensions and proportions to each other. For example, the housing may have four walls (top', 'bottom', 'front', and 'back'), but two of the long sides may be open, so that one can look through the housing into the page in the FIG. 3A side view. As described herein, the length of the housing side walls refers to the longer dimension of the open walls (also corresponding to the longer dimension of the top and bottom walls of the housing as illustrated in the Side View of FIG. 3A.) The height and width of the housing refers to the dimensions of the remaining sidewalls or the top and bottom walls as illustrated in the Front view of FIG. 3A. Dimensions provided below list the dimensions of the housing in the order of (length×width×height). The length of the housing may be at least two-times greater than the width and height dimensions. By way of a non-limiting example, the dimensions of the housing may be approximately 25×3.75×2.25 mm, with walls 0.5 mm thick. Housing 300 may be made of a hermetic, strong, and biocompatible material, such as ceramic. Such housings are fabricated with processes well known in the art, including micromachining, ultrasonic machining, wet etching, plasma etching, or laser machining. While examples are made to a cuboid housing, it will be appreciated that other shapes and configurations may be used, such as cylindrical housings, prism-shaped housings, octagonally or hexagonally cross-sectioned housings, or the like. Further, it will be appreciated that while a specific dimension, such as a length, may be discussed below with respect to the embodiments described herein, the ratios, comparisons, and descriptions set forth may apply to any dimensions, including length, width, height, or any other applicable dimension.

In other embodiments the length of the implant housing may have values of 5, 10, 15, 20, 25, or 30 mm long. The cross sections may have width×height values of 5×3 mm, 4.5×2.25 mm, 3.25×2.25 mm, 2.5×1.75 mm, or 2×1 mm.

In FIG. 3B, an antenna coil 14, also shown in cutaway, is placed into the housing 300 via the open walls on the long side. Microelectronics 301, which may include one or more pressure sensors, may also be placed inside housing 300, inside the region encircled by coil 14, or outside of this region.

FIG. 3C depicts the final step, in which thin walls 302 are bonded to housing 300, such as hermetically bonded. It will be appreciated that the thin walls 302 may be sealed or bonded in any appropriate manner. It will also be appreciated that the concepts herein may apply to non-hermetic housing applications, such as acute implants. In these cases, non-hermetic materials and bonding methods known in the art may be used. As illustrated and described in the examples herein, the thin walls 302 may be substantially thinner, or include a portion that is substantially thinner, than the remaining walls of the housing. Non-limiting examples of wall thicknesses of the housing walls and thin walls 302 are provided below. By orienting the thin walls 302 such that they are parallel to the axis 303 of coil 14, the width of coil 14 in the short dimension (left to right in the front view) is maximized. In this way, the implant package can achieve the maximum possible coil loop area within the width constraint imposed on the short dimension. It will be appreciated that the coil axis 303 refers to the central axis of a generally spirally wound coil 14, as shown in FIG. 3. The spirally wound coil 14 may be any appropriate shape, such as circular, rectangular, or any other shape.

The final implant produced by the process of FIG. 3 meets the complex requirements of medical implants: (i) small cross-sectional area, (ii) non-metal housing, (iii) hermetic sealing, (iv) biocompatibility, and (v) maximum internal volume for a given external volume.

In another embodiment, maximal internal height may be desirable also with small cross-sectional area. The implant packaged shown in FIG. 3 may also meet these requirements by rotating the housing 90 degrees so that the thin walls bond to both top and bottom surface of the housing rather than the sides.

In the case where wireless implant 20 contains a pressure sensor, internal electronics 301 may include one or more pressure sensors known in the art, and thin walls 302 may be flexible membranes which communicate pressure to internal electronics 301 by means of an incompressible fluid or gel that fills the cavity formed by housing 300 and thin walls 302. In another embodiment, the thin walls 302 may be flexible membranes which are part of a sensing electronic circuit, thus transducing pressure directly into an electronic signal of a sensing circuit.

The walls of the housing other than the thin walls 302 may be greater than 0.3 mm. By comparison, in an embodiment, by using membranes as the thin sidewalls 302 of the implant package 20 each sidewall may have a thickness of less than 0.15 mm. In another embodiment, by using membranes as the thin sidewalls 302 of the implant package 20 each sidewall may have a thickness less than about 0.050 mm. In another embodiment, by using membranes as the thin sidewalls 302 of the implant package 20 each sidewall may have a thickness of about 0.025 mm. In another embodiment, by using membranes as the sidewalls of the implant package 302 each sidewall may have a thickness less than about 0.025 mm, such as about 0.020 mm, about 0.015 mm, about 0.010 mm, about 0.005 mm, about 0.001 mm and any sized thickness in between. Thus, the thin walls 302 may have one half or less of the thickness of the non-thin walls of the housing 20.

In a typical embodiment, thin walls 302 may be made of one or more thin film materials such as glass, quartz, fused silica, titanium, silicon, sapphire, diamond, or others. It may be thinned by polishing, etching, or other methods well known in the art. Thin walls 302 may be bonded to housing 300 by several means known in the art, including laser welding, glass frit bonding, or compression bonding by brazing, soldering, or eutectic bonding, following deposition of a metal braze ring on the two surfaces.

For bonding technologies that require a metal ring to be deposited around the perimeter of each diaphragm, on both the diaphragm and mating surfaces on the housing, the architecture of FIG. 3C provides a further advantage over the prior art. When the metal ring is parallel to the antenna windings, as in prior art FIG. 1, it may absorb and dissipate significant amounts of energy going to and coming from the antenna 14, due to shielding and eddy current formation. However, when the diaphragm bonding rings are arranged perpendicular to the antenna windings as in FIG. 3C, the shielding and eddy current effects are practically eliminated.

The thin-walled housing or implant package 20 provides a significant improvement in the efficient use of space inside an implant package over prior art. By way of a non-limiting example, for a prior art implant package having an outer width of about 4 mm, the maximum available width for the antenna was approximately 3 mm. By contrast, in a thin-walled implant package 20 with an outer width of about 4 mm, the available width for the antenna is approximately 3.95 mm. Such an increase in antenna width for a given implant outer size may dramatically increase the wireless link distance of an implantable wireless sensor. This difference in antenna width of the thin-walled implant package 20 can translate into a catheter delivery system that is about 3 Fr sizes smaller for the present invention than for prior art systems. Similarly, if the implant housing is rotated 90 degrees, the thin-walled housing implant package may provide significantly more room for a tall antenna.

The invention is thus particularly useful in wireless implants that have one axis longer than the others, which is generally the case for implants that are intended for placement in blood vessels, or intended for delivery through a catheter device. If the ratio of length to width of such an implant is x, then increasing the coil's width dimension by n microns creates more coil area than the same increase in the length dimension, by a factor of x. In such wireless implants, one can generally maximize coil area by placing the thinnest sidewalls parallel to the coil axis, and perpendicular to the shorter dimension, as in FIG. 3C.

It will be further appreciated that the implant architecture can be used to maximize the size of any internal component, substance, or combination thereof. These may include, but are not limited to, drugs, steroids, batteries, stimulus electrodes, pacing circuitry, flow sensors, chemical sensors, or other electronics.

It will be further appreciated that although the exemplary embodiments depict a rectangular coil, the coil 14 can be generally circular, ovular, rectangular, or can take the form of any polygon that encloses an area. Additionally, although a rectangular housing is shown in the exemplary embodiment figures, the concept of disposing the thin walls on the outer periphery of coil 14, parallel to coil axis 303, can be generalized to any polygonal shape.

The disclosed invention depicted in FIG. 3 may have a further benefit for pressure sensing implants. Many commonly available chip-scale pressure sensors are well suited for use in wireless implants. However, such pressure sensors generally have small, thin, pressure sensing diaphragms, on the order of 2 mm diameter or less and thickness of 500 nm or less. If such a diaphragm is exposed to living tissue or blood, one or more layers of cells will usually grow on it after a period of several days or weeks. Cell layers such as this are known to stiffen the sensor's diaphragm, decreasing the device's sensitivity. In the embodiment shown in FIG. 3C, the thin sidewalls 302 may serve as flexible pressure diaphragms, which communicate pressure to chip-scale pressure sensors on internal electronics 301 through a pressure-communicating medium. Because they are larger in area and generally stiffer than the diaphragms of chip scale sensors, the thin sidewalls 302 will not be stiffened significantly by several layers of cell growth, compared to the smaller diaphragms of the chip-scale sensors. Thus the present invention allows pressure sensor implant designers to select from a number of available off-the-shelf or custom chip-scale pressure sensors, without having to worry about diaphragm stiffening due to cell growth.

While the thin-walled implant package 20 may be used with RF medical implants, the designs set forth herein are useful for any micro device or component where a nonmetal hermetic enclosure is required and where it is desirable to minimize sidewall thickness. Examples include, but are not limited to, sensors, actuators, or transponders located in harsh chemical environments, in liquid immersion, in high temperature zones (such as engines), or in environments where sterility is critical. Other examples include applications where the internal electronics must be hermetically housed, but cannot tolerate shielding or eddy current losses imposed by metal housings or braze rings. The designs and methods described herein overcome the many challenges associated with wireless sensors that use radiofrequency.

Figure 4A:
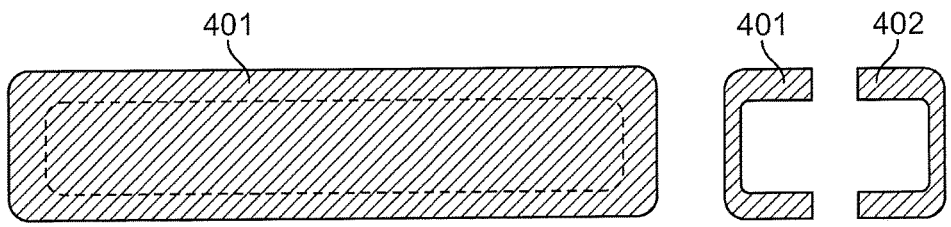
FIG. 4A illustrates the housing portion of an alternative embodiment of the present invention, with etched cavities and a split housing.
Figure 4B:
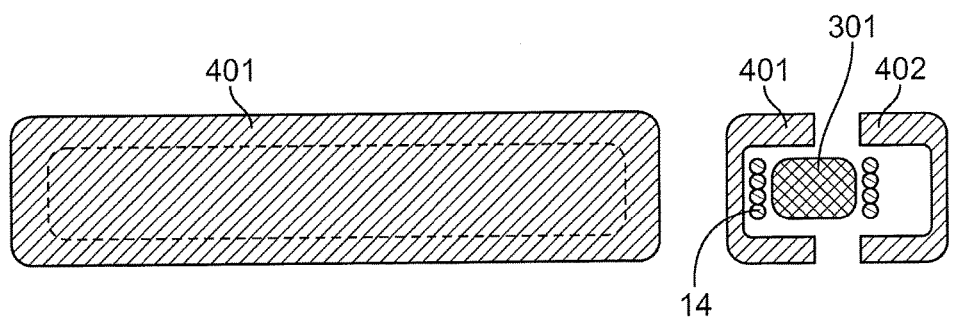
FIG. 4B illustrates the assembly of an alternative embodiment of the present invention, with etched cavities and a split housing.
Figure 4C:
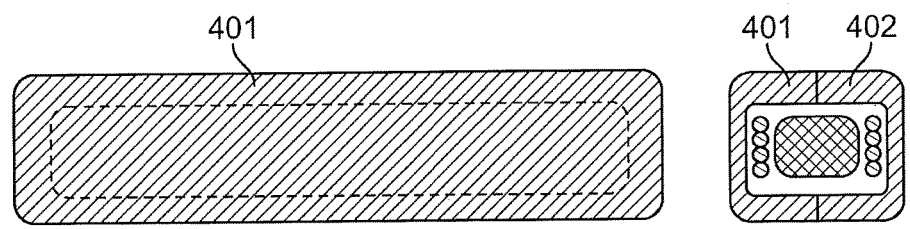
FIG. 4C illustrates the completed implant, for an alternative embodiment of the present invention, with etched cavities and a split housing.

There are also numerous variations of the embodiment shown in FIG. 3. For example, as shown in FIG. 4A, the housing is formed in two pieces 401 and 402, each with a cavity formed by one of the micromachining processes known in the art. The location of the cavity is shown as a dotted line in the side view, and can be seen in the cutaway. As shown in FIG. 4B, the coil 14, electronics 301, and other internals are inserted into one of the housing pieces 401. As shown in FIG. 4C, housing pieces 401 and 402 are bonded together hermetically by one of the methods previously disclosed. Note that in FIGS. 4A-4C, housing pieces 401 and 402 are shown as symmetrical, but asymmetrical pieces may also be employed.

Figure 5A:
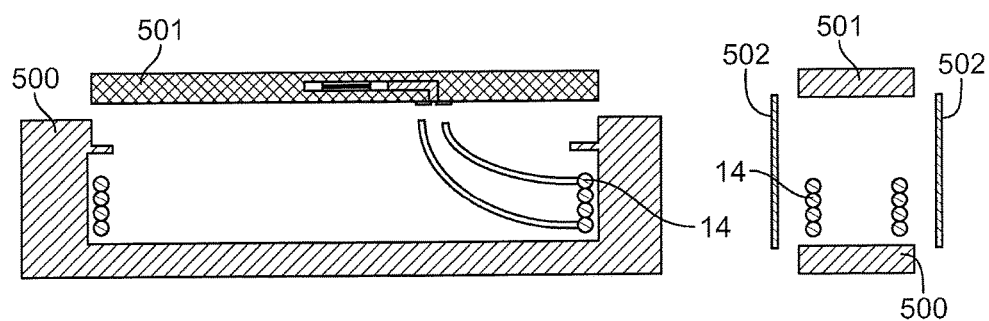
FIG. 5A is an exploded sketch of another alternative embodiment of the present invention, with electronics bonded to the top of the housing.
Figure 5B:
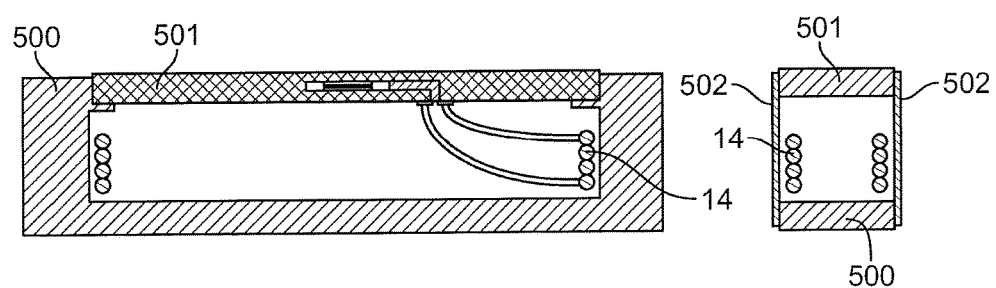
FIG. 5B illustrates the completed alternative embodiment of the present invention, with electronics bonded to the top of the housing.

FIGS. 5A and 5B depict an embodiment in which the electronics 501 are fabricated as a thin film device by one of the processes known in the art, with FIG. 5A being an exploded view and FIG. 5B showing all parts assembled. In FIGS. 5A and 5B, housing 500 has its long sides open as before, but this time its top side is open. Coil 14 is then inserted into housing 500. The thin film electronics device 501 is connected to coil 14 by wirebonding, conductive adhesive, or other means known in the art, and electronics 501 are then hermetically bonded to housing 500 using one of the aforementioned processes. Electronics 501 now forms the top surface of the housing. Thin sidewalls 502 are hermetically attached to housing 500 as before. If the thin electronics 501 contain a pressure sensor, the internal volume of the housing may not need to be filled with an incompressible fluid, as thin sidewalls 502 do not need to communicate pressure. Additionally, it will be appreciated that the steps of bonding electronics 501, bonding each of thin sidewalls 502, or inserting coil 14, may be done in a different order. The electronics 501 may be a single, solid state device, such as a capacitive sensor, or it may be multiple devices attached to a hermetic substrate such as LTCC.

Figure 6:
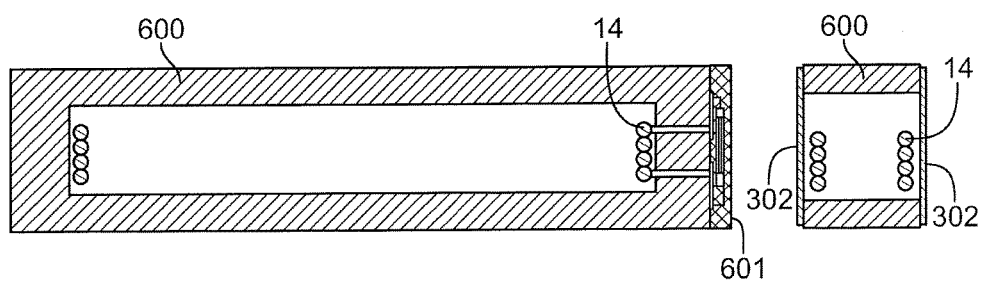
FIG. 6 illustrates another alternative embodiment of the present invention, with electronics bonded to the side of the housing.

FIG. 6 illustrates an embodiment similar to that of FIG. 5. The electronics 601 are placed on the exterior of housing 600, but this time on one of the short ends. FIG. 6 depicts hermetic electrical feedthroughs connecting electronics 601 to coil 14, but a 'free wire' connection method such as the one depicted in FIGS. 5A and 5B may also be employed. As in FIGS. 5A and 5B, the thin sidewalls 302 are not communicating pressure and so incompressible liquid fill may not be required.

Figure 7:
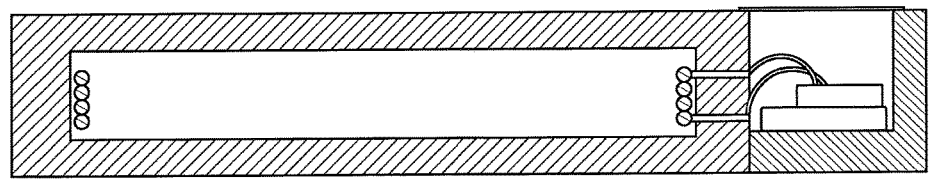
FIG. 7 illustrates another alternative embodiment of the present invention, with electronics contained in a separate housing chamber

FIG. 7 illustrates an embodiment similar to that of FIG. 6. Here the housing has two chambers, one for the coil and another for the electronics (shown here as "Sensor" and "Substrate"). The coil and electronics connect via a feedthrough that may or may not be hermetic. Thin sidewalls are placed in the usual place on the sides of the coil, and again over the chamber that contains the electronics. If the electronics does not contain a pressure sensor, the sidewall over the electronics chamber may be a thicker wall or a thin wall of a stiffer material. If the electronics contains a pressure sensor, and if the electrical feedthrough is sufficiently leak tight, then only the chamber containing the sensor needs to be filled with incompressible fluid.

The invention disclosed herein is particularly advantageous when the wireless implant is required to be long and narrow, as is typically the case with cardiovascular implants. With such geometries, any coil width gained in the short dimension has a dramatic impact on coil area and hence link distance. In other embodiments, it may be advantageous to use the present invention to increase the height of a coil inside the implant.

Many of the embodiments disclosed herein may benefit from having the final sidewalls attached in a vacuum environment, to prevent internal pressures inside the housing from varying with temperature. Alternatively, the internal volume may be filled with an inert gas to limit corrosion of the internals.

It will also be appreciated that the implant housing embodiments disclosed herein can be made using all thick walls, and then post-processing the housing to thin portions of the walls that are parallel to the coil's axis. State of the art post-processing technologies such as grinding, polishing, etching, or laser ablation are some possible means for accomplishing this.

Figure 8:
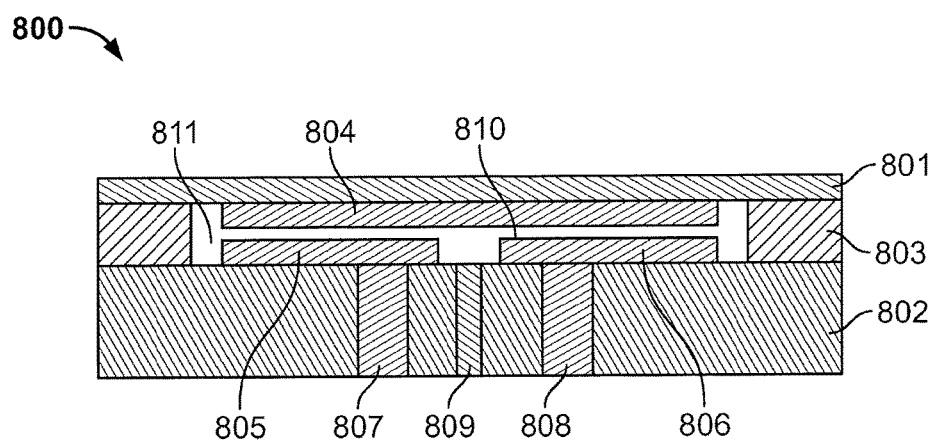
FIG. 8 illustrates an example pressure sensor.

FIG. 8 shows a cross sectional view of an example capacitive pressure sensor 800. While the capacitive pressure sensor 800 shown suggests a series capacitor design, other configurations of electrode connections are possible to create a single parallel plate capacitor design. In one embodiment the sensor 800 may be formed by bonding a lid wafer 801 to a base wafer 802. In some embodiments, an intermediary layer 803 may be used to bond lid wafer 801 and base wafer 802. In some embodiments, the intermediary layer 803 may be formed from the lid wafer 801 or base wafer 802. In some embodiments, the intermediary layer 803 may be electrically conducting and may electrically connect a lid electrode 804 to an electrical via on the base wafer. The lid wafer 801 includes at least one lid electrode 804. In one embodiment, the lid wafer includes two electrodes. In one embodiment, the base wafer 802 includes base electrode 805 and a second base electrode 806. Lid electrode 804 and base wafer electrodes 805 and 806 may be separated by a small gap 810 and sealed inside a cavity 811. The gap 810 may be on the order of 0.1-10 um, or approximately 1 um. A pressure applied to lid wafer 801 may cause the lid electrode 804 to move closer to or further from base electrodes 805 and 806 resulting in a change in capacitance of the capacitive pressure sensor 800. In one embodiment, base electrodes 805 and 806 may be a single electrode. Base electrode 805 has an electrical via 807 that allows electrical contact to the base electrode 805 outside of the cavity 811. Base electrode 806 has an electrical via 808 that allows electrical contact to the base electrode 806 outside of the cavity 811. In one embodiment, the electrical vias 807 and 808 pass through base wafer 802 to the underside of base wafer 802 and may have a surface amenable to wirebonding, soldering, flipchip, or other electrical attachment means. In another embodiment, the electrical vias 807 and 808 may be accessible outside the perimeter of the base wafer. In one embodiment, a port 809 allows fluid access to cavity 811. Port 809 may allow cavity 811 to be at equal pressure to surrounding medium. In one embodiment, lid wafer 801 and base wafer 802 are made of a ceramic, such as glass, and electrodes 804, 805, and 806 are made of a metal, such as gold. In one embodiment, electrical vias 807 and 808 are made of an electrically conducting material, such as copper, nickel, titanium, or highly doped silicon. Such a capacitive pressure sensor 800 and derivations thereof may be particularly useful for forming a wireless pressure sensor and integrated with an implant housing.

It will be appreciated that the term "wafer," as used above and herein, is a non-limiting term that could mean wafer, substrate, layer, or other similar phrases. It will be further appreciated that the embodiments of the invention described herein, as well as housing and wireless implant integration, may be performed at the die level or wafer scale, or some parts at wafer scale and some parts at die level.

Figure 9:
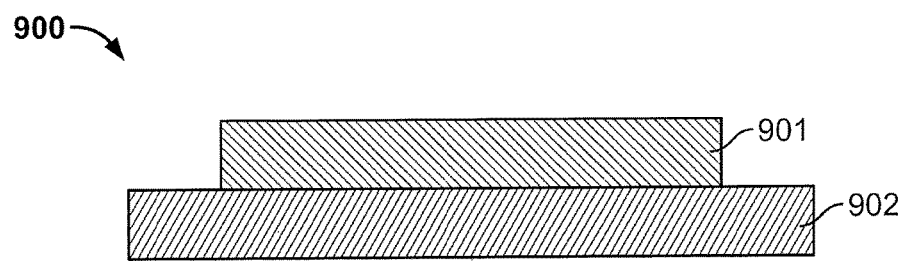
FIG. 9 illustrates an example pressure sensor where the base of the pressure sensor has at least one dimension that is longer than the lid of the pressure sensor.
Figure 10:
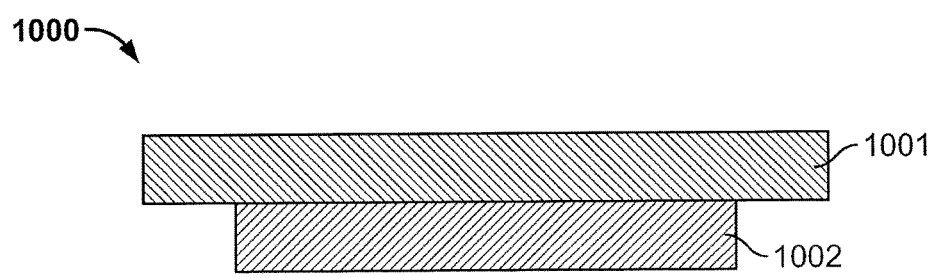
FIG. 10 illustrates an example pressure sensor where the lid of the pressure sensor has at least one dimension that is longer than the base of the pressure sensor.

FIG. 9 shows another embodiment of a capacitive pressure sensor 900, where lid wafer 901 may have at least one length that is shorter than a length of base wafer 902. FIG. 10 shows another embodiment of a capacitive pressure sensor 1000, where lid wafer 1001 may have at least one length that is longer than a length of base wafer 1002. The configurations of pressure sensors 900 and 1000 may allow for an implantable wireless pressure sensor with small cross sectional area. It should be appreciate that the lid wafer and base wafer may be of arbitrary thickness. In some embodiments, lid and base wafer may have a thickness from 10 um-1000 um.

Figure 11:
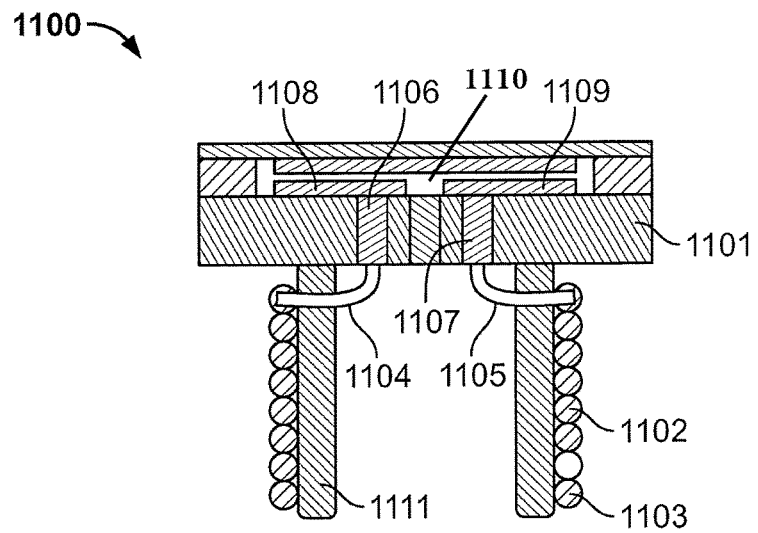
FIG. 11 illustrates a sensor electrically connected to an antenna.

FIG. 11 shows a wireless pressure sensor 1100 formed by electrically connecting capacitive pressure sensor 1101 to an antenna 1102. Antenna 1102 may be comprised of several turns of a coil 1103. A first end 1104 of antenna 1102 may be electrically connected to an electrical via 1106 that is electrically connected to electrode 1108 inside cavity 1110. A second end 1105 of antenna 1102 may be electrically connected to an electrical via 1107 that is electrically connected to electrode 1109 inside cavity 1110. In one embodiment, wireless pressure sensor 1100 is an LC resonant tank.

Wireless pressure sensor 1100 may be attached to a housing to form a hermetically sealed wireless pressure sensor. Some hermetic attachment methods may require high temperatures, such as an oven frit process or a direct glass welding process. Other hermetic attachment methods may employ use of laser bonds or laser frit bonds to localize heat of the bond so as not to damage sensitive electronics. In one embodiment, capacitive pressure sensor 1101 may be a MEMS pressure sensor constructed of glass and metal. In another embodiment, the sensor 1101 may be constructed of glass, metal, and silicon. In one embodiment, the sensor 1101 may be able to withstand high temperatures, such as temperatures greater than 300 C, or greater than 500 C, without damaging the sensor 1101. Such a sensor could be amenable to hermetic bonding to a glass housing via an oven frit weld process or a localized laser frit weld process. In one embodiment, the capacitive pressure sensor 1101 may be able to withstand hermetic bonding temperatures while the coil 1103, bobbin 1111, or other electrical circuitry may not be able to withstand hermetic bonding temperatures. The present invention describes several means of manufacturing an implantable wireless pressure sensor.

Figure 12:
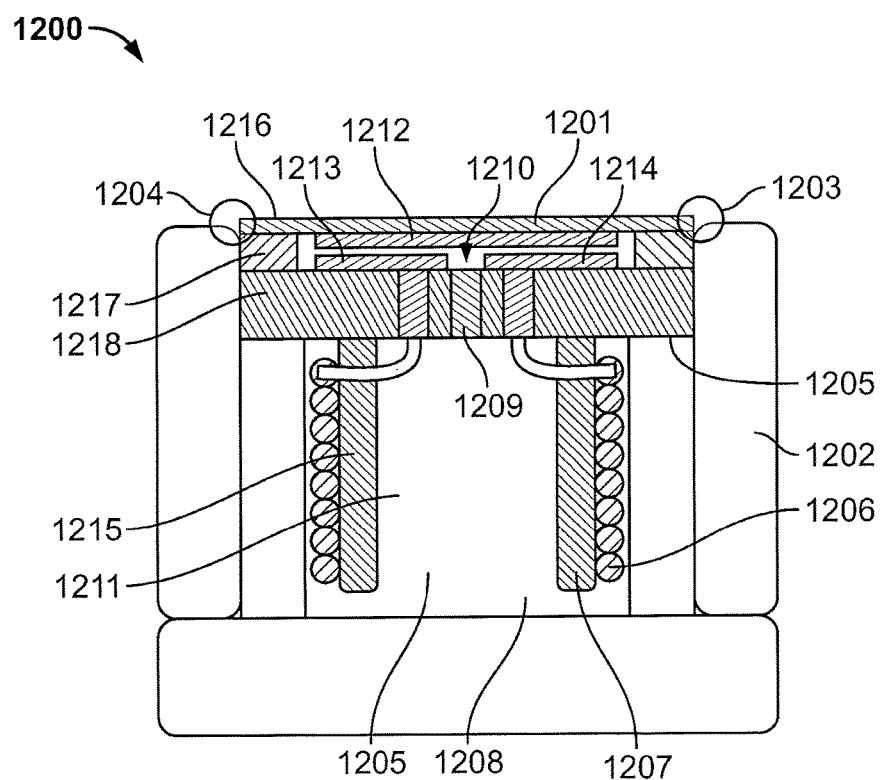
FIG. 12 illustrates one method of packaging the sensor into a wireless implant.

FIG. 12 shows an implantable wireless pressure sensor 1200. A wireless pressure sensor 1201 is inserted into a housing 1202. Part of the wireless pressure sensor 1201 may be bonded to housing 1202. The housing may have a ledge around the periphery. A variety of bonding methods may be employed. For an implantable wireless pressure sensor to function many years in the body, a hermetic bond is often desired. In one embodiment, the wireless pressure sensor 1201 may be bonded to the housing at bond locations 1203 and 1204. The bond may be a laser weld, a frit-laser weld, a frit weld, or other bonds known in the art. The wireless pressure sensor 1201 may rest on the ledge 1205 or it may be bonded at bond locations 1203 and 1204 and hang suspended over the ledge 1205. Bond locations 1203 and 1204 may be positioned at sufficient distance from electrodes 1212, 1213, 1214, coil 1206, and bobbin 1215 such that heat localized at the bond locations 1203 and 1204 does not reach sufficient temperatures to damage other components. Bond locations 1203 and 1204 may be optically clear to a laser path to allow for laser bonding at or below bond locations 1203 and 1204 so that wireless pressure sensor 1201 may be hermetically bonded to housing 1202. At least a portion of lid wafer 1216, intermediate layer 1217, and base wafer 1218 may be optically clear to allow laser energy to pass through without heating up the lid wafer 1216, intermediate layer 1217, and base wafer 1218. Laser energy may be focused at the interface of base wafer 1218 and housing ledge 1205 to form a hermetic bond. An intermediate layer may be placed on or near the housing ledge 1205, base wafer 1218 or lid wafer 1216 to absorb applied energy and form a hermetic bond between the capacitive pressures sensor 1201 and housing 1202.

The antenna 1206 on bobbin 1207 may rest on the inner housing bottom 1208 or it may hang suspended over the inner housing bottom 1208. The cavity 1210 of the wireless pressure sensor 1201 may be vented by port 1209 such that cavity 1210 is in fluid communication with cavity 1211 of the housing 1202.

Figure 13:
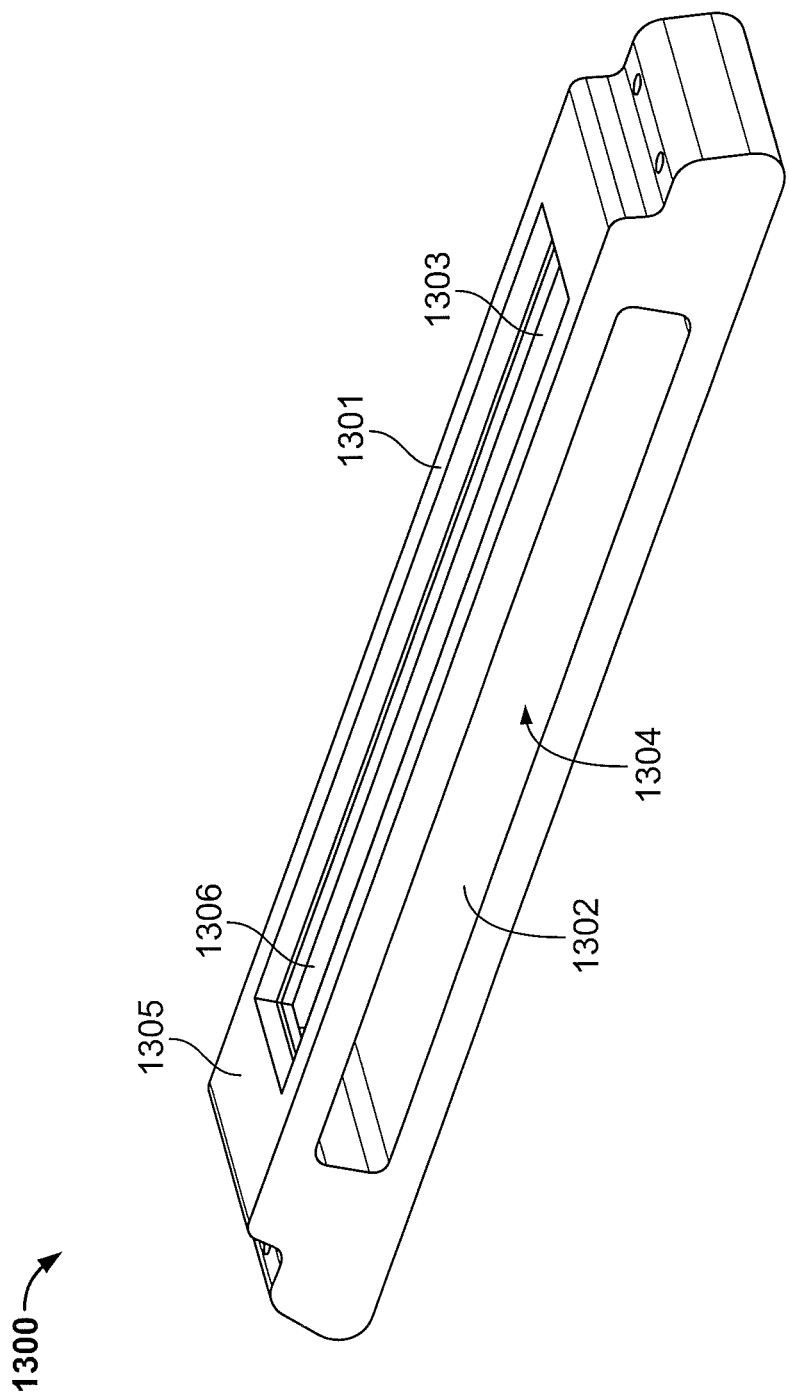
FIG. 13 illustrates an example housing for packaging a sensor into a wireless implant.

FIG. 13 shows a perspective view of a housing 1300 suitable for forming an implantable wireless pressure sensor. Housing 1300 may have a ledge 1301 recessed from a top surface 1305. Housing may have a through slot with open face 1302 on one side and open face 1303 on the opposite side. Housing may have a bottom wall 1304 beneath a top opening 1306. Electronics may be inserted into the housing in a variety of locations and sequences. A capacitive pressure sensor may be bonded to the top surface 1305 or ledge 1301. An antenna or other electronics may inserted into the housing via open face 1302 or open face 1303, or even from top opening 1306. In one embodiment, the housing may also have a slot through bottom wall 1304 to allow another opening for electronics insertion or thin wall attachment. Walls may be attached to cover open face 1302 or 1303 after electronics are inserted. There are several manufacturing approaches to assembling a wireless pressure sensor and sealing it inside a housing.

Figure 14:
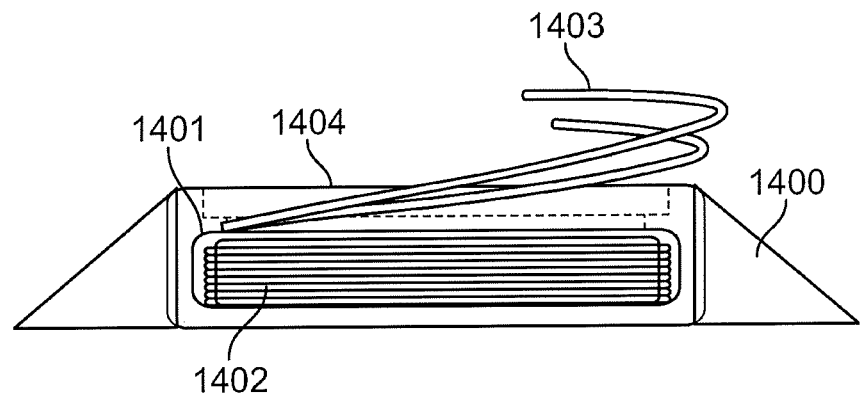
FIG. 14 illustrates a method of packaging a sensor into a wireless implant, where an antenna coil is inserted into the center cavity of an implant housing.

FIGS. 14-17 illustrate embodiments of forming a wireless pressure sensor in a housing. FIG. 14 illustrates a housing 1400 with a through slot 1401 on the housing side. An electronics assembly 1402 with coil ends 1403 is inserted in the through slot 1401 to reside in the housing 1400. Coil ends 1403 may be tucked inside the electronics assembly 1402 during insertion in through slot 1401. Coil ends 1403 may then be brought through the top slot 1404 in the housing 1400 so that coil ends are accessible through top slot 1404 of housing 1400. In this way, electronics assembly 1402 and coil ends 1403 are fully inside the perimeter of the housing 1400.

Figure 15:
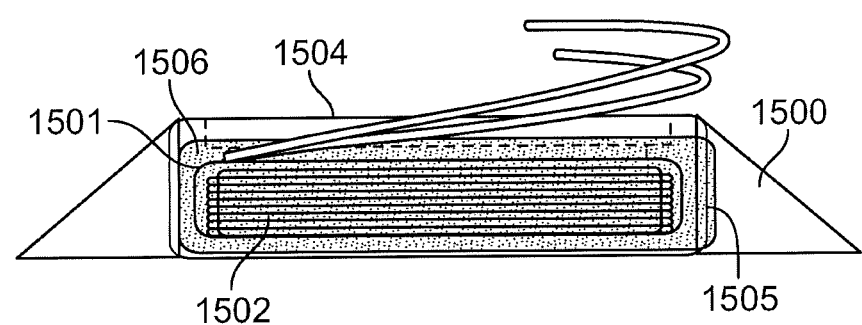
FIG. 15 illustrates a method of packaging a sensor into a wireless implant, where walls are bonded to the sides of an implant housing.

FIG. 15 shows a side walls 1505 attached to the housing 1500. The electronics assembly 1502 may be comprised of high temperature resistant ceramics or metals amenable for side walls 1505 to be hermetically attached to housing 1500 via a high temperature bonding process. In another embodiment, electronics assembly 1502 may be comprised of polymers or other materials that cannot withstand high temperatures. In one embodiment, side walls 1505 may be hermetically bonded to housing 1500 with a localized heating method, such as laser welding or laser frit welding along a perimeter of slot 1501 on the housing side surface 1506. In one embodiment, after side walls 1505 are bonded, the housing 1500 may have hermetic walls on all sides except for top slot 1504.

Figure 16:
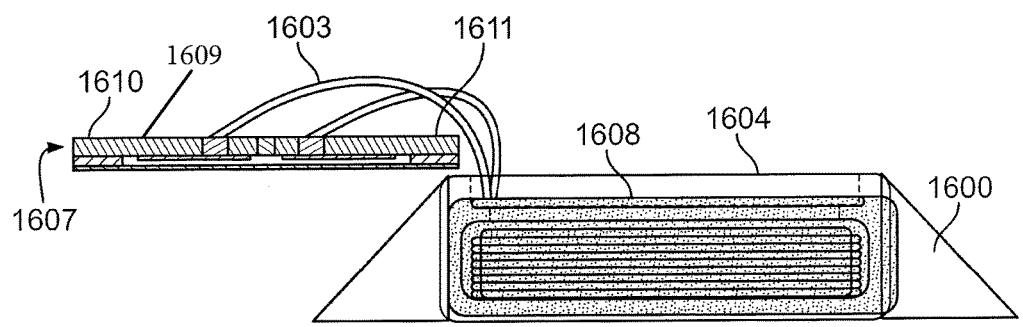
FIG. 16 illustrates a method of packaging a sensor into a wireless implant, where electrical connections from a circuit or electrical component inside an implant housing are connected to a sensor or circuit element exterior the housing.

FIG. 16 shows a capacitive pressure sensor 1607 electrically connected to coil ends 1603 that pass through top slot 1604. The housing 1600 may have a ledge 1608 suitable for resting a bottom surface 1609 of capacitive pressure sensor 1607. An intermediary material such as a glass frit, epoxy, or other bonding material may be applied to ledge 1608. The ledge 1608 may be along a small section of the perimeter of the housing such that the section has sufficient strength to support the capacitive pressure sensor 1607 and sufficient area for laser assisted or other bonding along the perimeter 1610 and 1611 of the capacitive pressure sensor 1607.

In other embodiments, an intermediate printed circuit board (PCB) may be bonded directly to coil ends 1603 or capacitive pressure sensor 1607 so that solder bumps may form one or more of the electrical connections. In another embodiment, a flex PCB may also be used. A surface mount capacitor may be added to the PCB or directly to capacitive pressure sensor 1607. In another embodiment, capacitive pressure sensor 1607 to may be bonded first to housing 1600 prior to insertion of electronics assembly and attachment of side walls.

Figure 17:
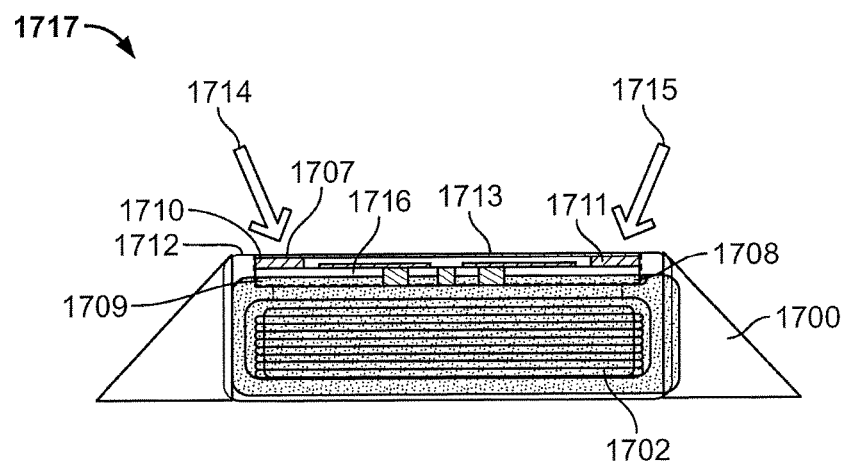
FIG. 17 illustrates a method of packaging a sensor into a wireless implant, where the sensor is bonded to the housing.

FIG. 17 shows capacitive pressure sensor 1707 bonded to housing 1700 at ledge 1708. It should be appreciated that capacitive pressure sensor 1707 may be bonded at another location of housing 1700 such as the top surface 1712 of housing 1700. In one embodiment, top surface 1713 of capacitive pressure sensor 1707 is flush with top surface 1712 of housing 1700. In other embodiments, top surface 1713 of capacitive pressure sensor 1707 may sit below or stand proud above top surface 1712 of housing 1700. In one embodiment, localized bonding processes, such as with light or heat or other means, may be applied along perimeter locations 1714 and 1715. In one embodiment, bonding along perimeter locations 1714 and 1715 allows bonding to occur at the bottom surface 1709 of capacitive pressure sensor 1707. In one embodiment, laser energy applied along perimeter locations 1714 and 1715 passes through capacitive pressure sensor 1707 at perimeter locations 1710 and 1711 such that the bond between capacitive pressure sensor 1707 and housing 1700 occurs at the interface of the ledge 1708 of housing 1700 and the bottom surface 1710 of capacitive pressure sensor 1707. In one embodiment, laser energy may directly bond capacitive sensor 1707 to housing 1700. In another embodiment, an intermediary layer may be used to bond capacitive sensor 1707 to housing 1700. In an embodiment, a localized bonding process may allow for a hermetic seal between capacitive pressure sensor 1707 and housing 1700 without damaging electronics assembly 1702 or electronic elements 1716. A hermetically sealed wireless sensor 1717 may be manufactured in similar means. It should be appreciated that in other embodiments, the wireless sensor may incorporate sensitive biologic, chemical, optical, or other elements to allow for sensing of a variety of metrics.

Figure 18:
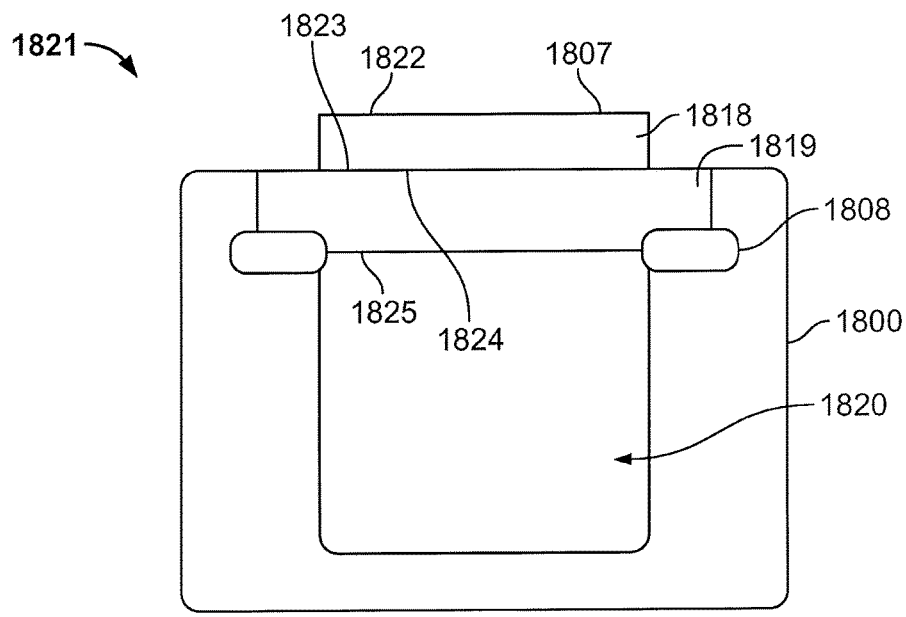
FIG. 18 illustrates one method of attaching a sensor to a housing.

FIG. 18 illustrates another means of forming a hermetically sealed cavity 1820 inside a housing 1800 with a capacitive pressure sensor 1807 interfacing with the surroundings 1821. In one embodiment, housing 1800 may have a ledge 1808 suitable for supporting and/or bonding a portion of capacitive pressure sensor 1807 to housing 1800. It should be appreciated that capacitive pressure sensor 1807 may be bonded to a top surface of the housing 1800 or another surface of the housing 1800. Capacitive pressure sensor 1807 may be comprised of at least two layers, where a lid wafer 1818 may comprise one layer and a base wafer 1819 may comprise a second layer. Lid wafer 1818 may have at least one dimension smaller than a dimension of base wafer 1819. Lid wafer 1818 may have a first surface 1822 exposed to the surroundings 1821 and a second surface 1823 exposed to a first surface 1824 of the base wafer 1819. The base wafer 1819 may have a second surface 1825 exposed to the cavity 1820 in the interior of housing 1800. Electronics, metals, or other sensing elements may reside in a location between second surface 1823 of lid wafer 1818 and first surface 1824 of base wafer 1819. The perimeter of lid wafer 1818 may be hermetically bonded to base wafer 1819. Electrical vias through the base wafer 1819 may provide electrical connection to the cavity 1820 in the interior of housing 1800 with electrical features on the first surface 1824 of base wafer 1819 or with electrical features on the second surface 1823 of lid wafer 1818. The electronic elements may all reside in hermetic seals. In an embodiment, an antenna may reside inside the cavity 1820 of housing 1800 and electrically connect to capacitive pressure sensor 1807 to form a hermetically sealed wireless pressure sensor.

Figure 19:
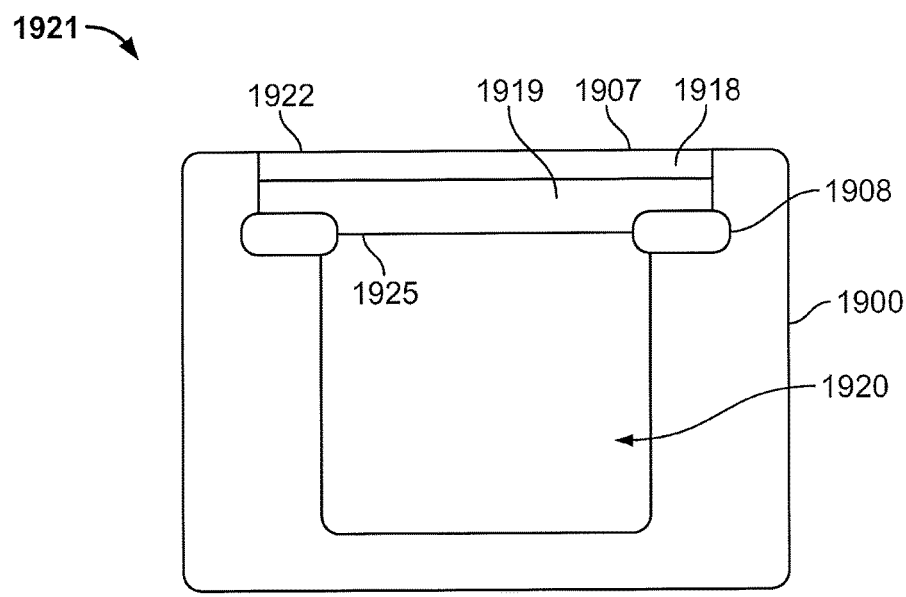
FIG. 19 illustrates another method of attaching a sensor to a housing.

FIG. 19 illustrates a similar embodiment of forming a hermetically sealed cavity 1920 inside a housing 1900 with a capacitive pressure sensor 1907 interfacing with the surroundings 1921. In the embodiment shown, lid wafer 1918 may be thinner than base wafer 1919. It should be appreciated that a variety of thicknesses may be utilized for lid wafer 1918 and base wafer 1919 such that wafers 1918 and 1919 are of equal or different thickness. In one embodiment, a first surface 1922 of lid wafer 1918 may sit flush with a top surface of housing 1900. In one embodiment, at least a portion of the perimeter of base wafer 1919 is bonded to the housing 1900 along a ledge 1908, where a bond is formed at the second surface 1925 of base wafer 1919 and a surface of the housing 1900. In an embodiment, an antenna may reside inside the cavity 1920 of housing 1900 and electrically connect to capacitive pressure sensor 1907 to form a hermetically sealed wireless pressure sensor.

Figure 20:
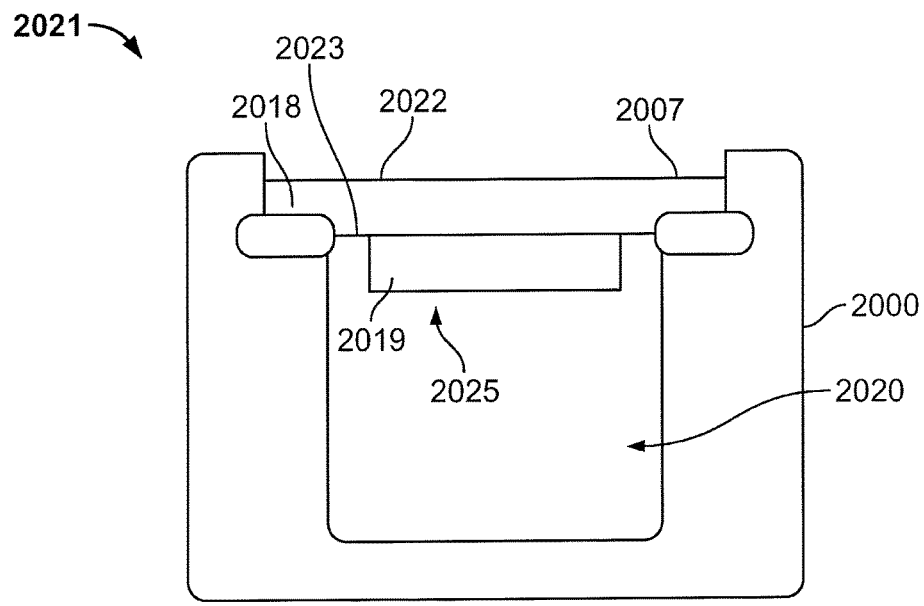
FIG. 20 illustrates another method of attaching a sensor to a housing.

FIG. 20 illustrates another embodiment of forming a hermetically sealed cavity 2020 inside a housing 2000 with a capacitive pressure sensor 2007 interfacing with the surroundings 2021. In one embodiment, base wafer 2019 is hermetically sealed inside the cavity 2020 of housing 2000. In an embodiment, lid wafer 2018 may be comprised of a glass material and base wafer 2019 may be comprised of a glass material or silicon. The silicon may be of high resistivity, such as float zone silicon. The first surface 2022 of the lid wafer 2018 may sit flush with the top surface of housing 2000, recessed below, or stand proud above. The capacitive pressure sensor 2007 may be electrically connected to elements inside the cavity 2020 by electrical connections at the second surface 2023 of the lid wafer 2018 or by electrical connections at the second surface 2025 of the base wafer 2019. In an embodiment, an antenna may reside inside the cavity 2020 of housing 2000 and electrically connect to capacitive pressure sensor 2007 to form a hermetically sealed wireless pressure sensor.

Figure 21:
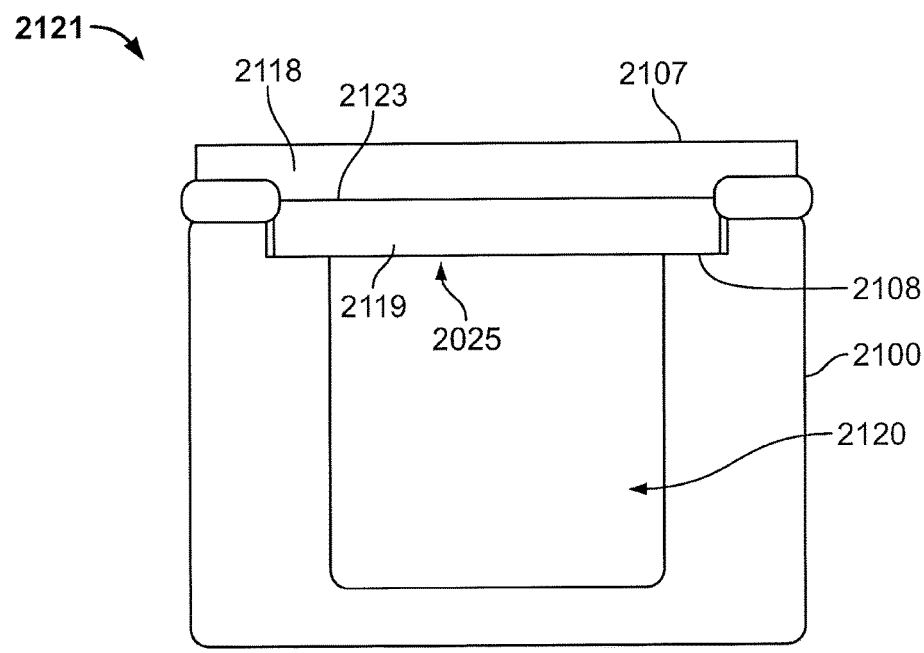
FIG. 21 illustrates another method of attaching a sensor to a housing.

FIG. 21 illustrates another embodiment of forming a hermetically sealed cavity 2021 inside a housing 2100 with a capacitive pressure sensor 2107 interfacing with the surroundings 2121. In this embodiment, portions of the second surface 2123 along the perimeter of lid wafer 2118 are bonded to the housing 2100. Base wafer 2119 may rest on a ledge 2108 in housing 2100 or base wafer 2119 may be suspended above ledge 2108. In an embodiment, an antenna may reside inside the cavity 2120 of housing 2100 and electrically connect to capacitive pressure sensor 2107 to form a hermetically sealed wireless pressure sensor.

Figure 22:
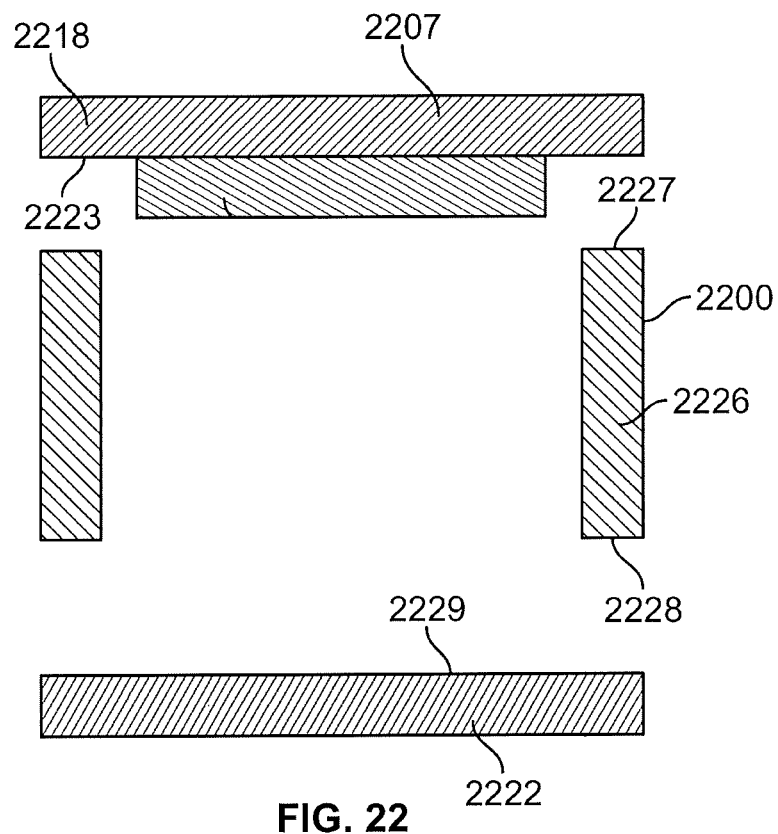
FIG. 22. illustrates a sensor, a housing, and a wall in an exploded view.
Figure 23:
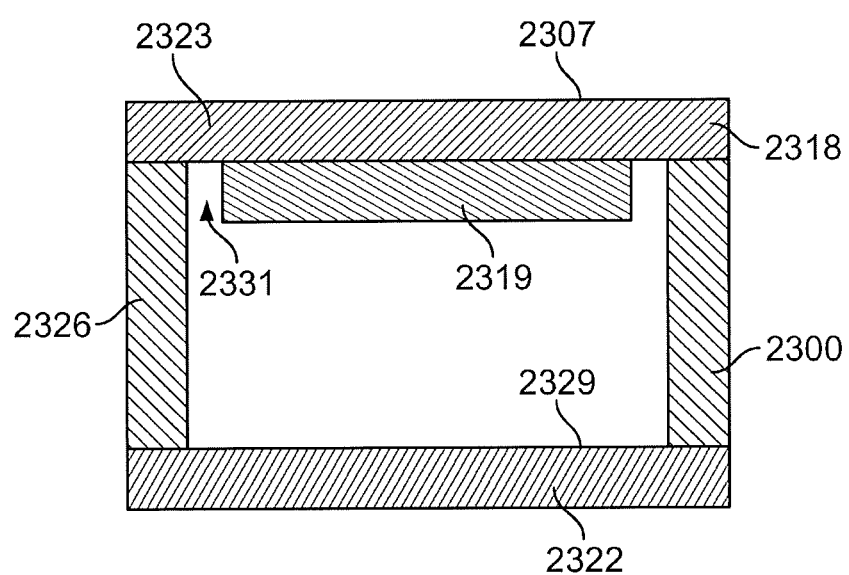
FIG. 23 illustrates another method of attaching a sensor and a wall to a housing.

FIGS. 22 and 23 illustrate another embodiment of forming a hermetically sealed cavity inside a housing with a capacitive pressure sensor interfacing with the surroundings. FIG. 22 shows an exploded cross sectional view of such an embodiment whereas FIG. 23 shows an assembled cross sectional view of such an embodiment. The housing 2200 may have a through slot from top to bottom. The housing 2200 may have thin sidewalls 2226 or the sidewalls 2226 may be initially thick and later made thin by post-processing the housing 2200. State of the art post-processing technologies such as grinding, polishing, etching, or laser ablation are some possible means for accomplishing this. To form a hermetically sealed cavity with housing 2200, in one embodiment a capacitive pressure sensor 2207 may be bonded to a top surface of housing 2200 and a wall 2222 may be bonded to a bottom surface of housing 2200. In one embodiment, a second surface 2223 of capacitive lid wafer 2218 is bonded to a top surface 2227 of housing 2200. A first surface 2229 of wall 2222 is bonded to a bottom surface 2228 of housing 2200.

In one embodiment, capacitive pressure sensor 2207 is bonded to housing 2200 with a high temperature process. In one embodiment, an electronics assembly may be inserted through opening in bottom of housing to attach to capacitive pressure sensor 2207 prior to wall 2222 being bonded to housing 2200. In one embodiment, wall 2222 may be bonded to housing 2200 using a localized bonding method to avoid damaging electronics inside housing 2200.

FIG. 23 shows a hermetically sealed housing 2300 with capacitive pressure sensor 2307 at one surface of the housing 2300 and a wall 2322 at another surface of the housing. Such a manufacturing approach may be amenable to maximizing internal volume of a hermetically sealed cavity for a wireless pressure sensor. Lid wafer 2318 and wall 2322 may be made thin, such as having a thickness from 25 to 250 microns. Base wafer 2319 may also be made thin, and may have a width or length dimension that allows room for electronics in the space 2331 between base wafer 2319 and side wall 2326 of housing 2300. For example, space 2331 may be sufficient to allow turns of a coil antenna to be stacked vertically from the first surface 2329 of wall 2322 up to the second surface 2323 of lid wafer 2318.

Figure 24:
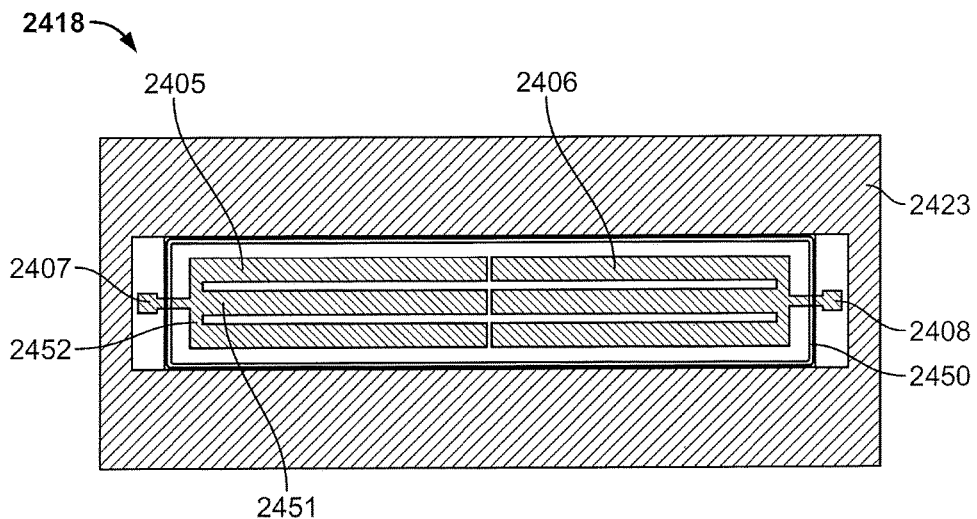
FIG. 24 illustrates a view of a capacitive pressure sensor including the top electrode of a capacitive pressure sensor and contact pads to a top electrode and a bottom electrode (not shown).
Figure 25:
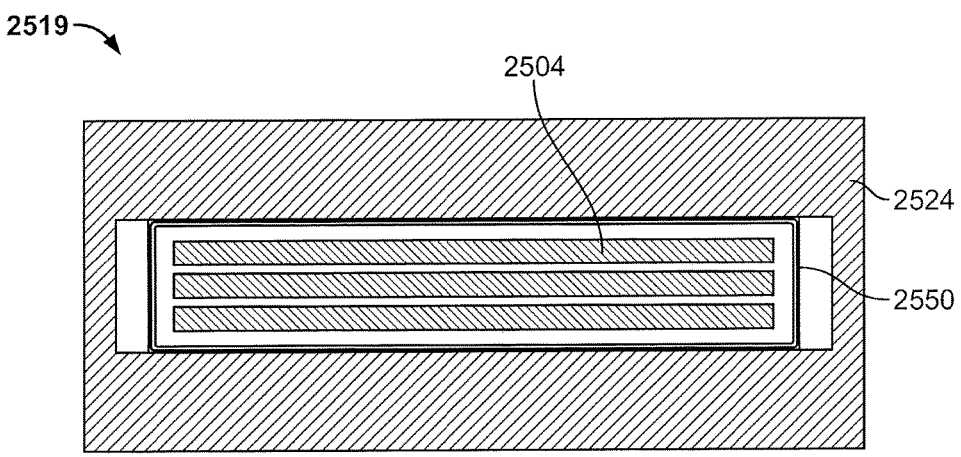
FIG. 25 illustrates a view of a bottom electrode of the capacitive pressure sensor of FIG. 24.
Figure 26:
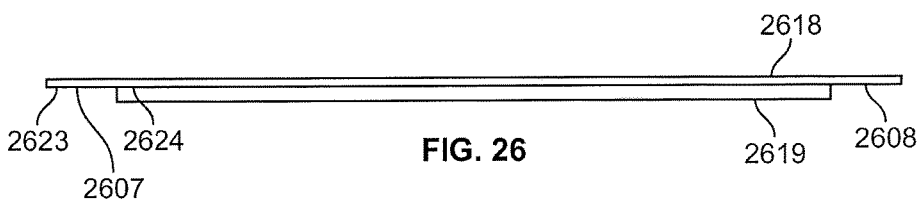
FIG. 26 illustrates a view of a top electrode of a capacitive pressure sensor.

FIGS. 24-26 illustrate a capacitive pressure sensor suitable for use in the implantable sensor configuration shown in FIGS. 22 and 23. FIG. 24 shows a second surface 2423 of lid wafer 2418. A first electrode 2405 and a second electrode 2406 are on the second surface 2423. A bond line 2450 around the electrodes is shown. When the bond line is bonded to another surface, the electrodes can be hermetically sealed or otherwise sealed inside the bond line 2450. Electrical vias 2407 and 2408 may pass underneath bond line 2450 to allow electrical contact to electrodes 2405 and 2406 on second surface 2423 of lid wafer 2418. While the present embodiment shows two electrodes, it should be appreciated that one or more electrodes may be formed on lid wafer 2418.

FIG. 25 shows a first surface 2524 of base wafer 2519. An electrode 2504 is on the first surface 2524 of base wafer 2519. The electrode 2504 may be fully contained within bondline 2550. Base wafer 2519 may have at least one length dimension smaller than lid wafer 2418. FIG. 26 shows lid wafer 2618 bonded to base wafer 2619. Second surface 2623 of lid wafer 2618 may be bonded to first surface 2624 of base wafer 2619. Electrical vias 2607 and 2608 may be accessible on the second surface 2623 of lid wafer 2618 while electrodes may be located within a bond line in between lid wafer 2618 and base wafer 2619. It will be appreciated that direct electrical contact may be made between lid wafer 2618 and base wafer 2619 so that electrical vias 2607 may provide direct electrical contact to elements on the base wafer 2619. Such a configuration described in FIGS. 24-26 would form a series capacitive pressure sensor that may be attached to an electronics assembly with coil and integrated into a hermetically packaged housing to form a hermetically sealed wireless pressure sensor. In other embodiments, a single parallel plate capacitive pressure sensor could be formed in a similar manner.

The electrode layout shown in FIGS. 24 and 25 has advantages over prior art electrode designs of large area solid plate electrodes. Large solid area electrodes of a capacitor when not positioned away from the inductor result in reduced quality factor of an LC circuit due to eddy currents in the capacitor electrode when the electrode is subject to high frequency alternating currents. The electrode layout shown in FIGS. 24 and 25 is comprised of conductive features over a solid area that incorporate slots or otherwise breaks that result in a non-continuous solid area. The solid area is broken into several narrow rectangular areas 2451 which are connected with thin a trace 2452. Such an electrode design can provide sufficient capacitance in a circuit yet is optimally design to present eddy currents which could reduce the quality factor of a wireless circuit.

Figure 27:
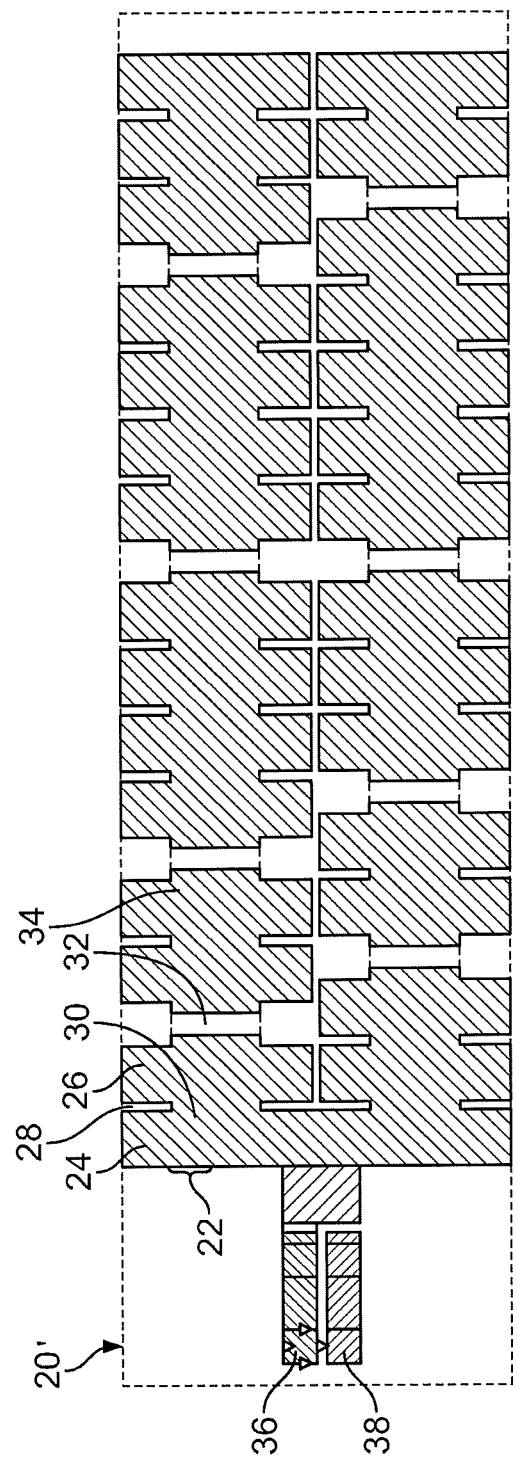
FIG. 27 illustrates a view of a bottom electrode of a capacitive pressure sensor.
Figure 28:
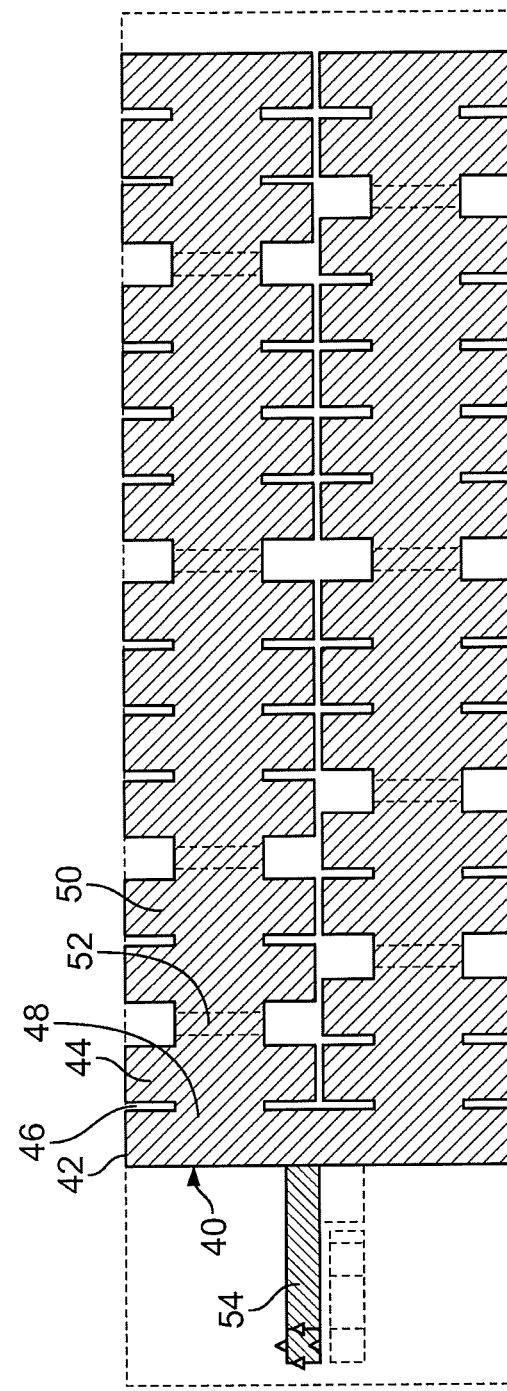
FIG. 28 illustrates a cross sectional view of a capacitive pressure sensor.

Figures 27 and 28 show another configuration of capacitor electrodes to optimize quality factor of a wireless circuit. In another embodiment, the electrodes may be configurable. Figure 27 shows a view of a configurable capacitor electrode. Electrical connections may be applied at the underside of the wafer to select which electrode areas are part of the circuit capacitance. Figure 28 shows a view of a capacitor electrode.

FIG. 27 is a view of a capacitive pressure sensor 20' with a configurable capacitor electrode 22. The electrode 22 is patterned in a specific configuration so as to reduce and effectively eliminate electrical eddy currents that may arise when the sensor is resonating at high frequency. Reducing electrical eddy currents in the capacitor electrodes increases the quality factor of the LC sensor. The patterned configurable electrode 22 thus provides for a high quality factor LC sensor in a compact configuration. The configurable electrode 22 includes rectangular patterns 24 and 26 that are spaced apart by a distance 28. The rectangular patterns 24 and 26 are electrically connected by a central member 30. In one embodiment, the rectangular patterns 24 and 26 can be 0.1 to 1 mm tall and 0.1 to 1 mm wide, the distance 28 can be 0.01 to 0.1 mm, and the central member 30 can be 0.1 to 1 mm tall and 0.01 to 0.1 mm wide. Many rectangular patterns 24 and 26 can be electrically connected to form a large area capacitor electrode 22. While rectangular patterns have been described, a variety of shapes and sizes may be utilized.

The capacitive pressure sensor 20' may optionally have electrically conducting areas that are not initially electrically connected to the top capacitor electrode 22. A gap 32 initially separates configurable electrode 22 from additional conducting areas 34. In one embodiment, a conducting material may be deposited in gap 32 to electrically connect top electrode 22 to additional conducting area 34. In another embodiment, thru wafer vias and contacts on the backside of a wafer may be connected to or not connected to to select additional conducting areas to add to the electrical circuit. This configurability allows tuning of both fixed and variable capacitance in the circuit after sensor fabrication. By electrically connecting the additional conducting areas 34 to the configurable electrode 22, the area of the configurable electrode 22 is increased in a controllable manner.

By modifying the configurable electrode 22, it is possible to change the capacitance of the capacitive pressure sensor 20' when the sensor 20' has an appropriately designed fixed capacitor electrode 40 (see FIG. 28). FIG. 28 shows a top view of the fixed capacitor electrode 40 of the capacitive pressure sensor 20'. The fixed electrode 40 is patterned in a specific configuration so as to reduce and effectively eliminate electrical eddy currents that may arise when the sensor is resonating at high frequency. Reducing electrical eddy currents in the capacitor electrodes increases the quality factor of the LC sensor. The patterned fixed electrode 40 thus provides for a high quality factor LC sensor in a compact configuration. The fixed electrode 40 can include patterns, such as rectangular patterns 42 and 44 that are spaced apart by a distance 46. The rectangular patterns 42 and 44 are electrically connected by a central member 48. Additional rectangular patterns 50 are electrically connected to rectangular patterns 42 and 44 by a central member 52. As shown in FIG. 15, the fixed electrode 40 includes several patterns that are all initially electrically connected. Due to this fixed electrode 40 configuration, when the gap 32 on top electrode 22 is filled with electrically conducting material to connect configurable electrode 22 to additional conducting area 34, the total capacitance of capacitive pressure sensor 20' is increased.

Optionally, an electrically conducting trace 54 connects the fixed electrode 40 to a probe pad 36 on the exterior surface of the capacitive pressure sensor 20'. A probe pad 38 on the exterior surface of the capacitive pressure sensor 20' connects to the configurable electrode 22. The probe pads 36 and 38 may be used to connect other circuit elements to the capacitive pressure sensor 20'.

It should be appreciated that a variety of sensors, not just pressure sensors, may be described by the embodiments of the present invention.

In all embodiments, the external housing may be surface treated with a biocompatible material to limit clot formation, control cell growth, or improve lubricity. Such materials may include heparin, silicone, parylene, cell tissue monolayers, or other coatings well known to those of ordinary skill in the art. Other materials may be applied or coated onto the housing to improve overall shape for flow dynamics, improved deliverability, or other features. Additional mechanical features may be attached to the housing to facilitate implantation in a desired location in the body. Many such features are disclosed in PCT Patent Application No. PCT/US2011/45583 entitled Pressure Sensor, Centering Anchor, Delivery System and Method, which is also incorporated herein by reference.

While the apparatus and method of subject invention have been shown and described with reference to preferred embodiments, those skilled in the art will readily appreciate that changes and/or modifications may be made thereto without departing from the spirit and scope of the subject invention.

Having thus described the invention, we claim:

1. A circuit comprising:
a housing having a plurality of walls that defines a cavity and an opening;
a sensor connected to said opening in said housing, said sensor comprising:
a lid wafer including at least one electrode and having a first dimension;
a base wafer including at least one electrode and being bonded to said lid wafer, said base wafer having a second dimension shorter than said first dimension; and
wherein said base wafer is positioned entirely within said cavity defined by said housing and a surface of said lid wafer is exposed to an exterior of said housing.

2. The circuit of claim 1, wherein said sensor is a pressure sensor.

3. The circuit of claim 2, wherein said pressure sensor is a capacitive pressure sensor.

4. The circuit of claim 1, wherein said sensor is connected to said opening to hermetically seal said housing.

5. The circuit of claim 1, wherein a second surface of said lid wafer is accessible from inside said housing.

6. The circuit of claim 1, wherein said lid wafer, said base wafer, and said housing are comprised of any combination of glass, silicon, or ceramic.

7. The circuit of claim 1, wherein an antenna is located within said housing.

8. The circuit of claim 7, wherein an antenna axis is substantially parallel to at least one wall of said housing.

9. The circuit of claim 1, wherein said circuit is configured to be implanted in a blood vessel.

10. The circuit of claim 1, wherein said housing is filled with a substance selected from a group including: liquid, gel, vacuum, inert gas, or air.

11. The circuit of claim 1, wherein the sensor is a capacitive pressure sensor wherein a second surface of said lid wafer is bonded to a first surface of said base wafer.

12. The circuit of claim 11, further comprising at least one electrical contact on said second surface of said lid wafer.

13. The circuit of claim 12, further comprising at least one electrical contact on said first surface of said base wafer wherein the at least one electrical contact on said second surface of said lid wafer and said at least one electrical contacts on said first surface of said base wafer are contained within a bondline.

14. A circuit comprising:
a housing having a plurality of walls that defines a cavity and an opening;
a sensor connected to said opening to form a hermetic seal in said housing, said sensor comprising:
a lid wafer having a first dimension, a first surface, and a second surface wherein said first surface is exposed to an exterior of said housing, at least one electrode positioned on said second surface of said lid wafer;
a base wafer having a first surface bonded to said second surface of said lid wafer and having a second dimension shorter than said first dimension, at least one electrode positioned on said first surface of said base wafer; and
wherein said at least one electrode on said second surface of said lid wafer and said at least one electrode on said first surface of said base wafer are contained within a bondline defined between the base wafer and the lid wafer; and
wherein said base wafer is positioned entirely within said cavity defined by said housing.

15. The circuit of claim 14 further comprising a cavity between the lid wafer and base wafer.

* * * * *